(12) United States Patent
Clapés Saborit et al.

(10) Patent No.: US 10,683,493 B2
(45) Date of Patent: Jun. 16, 2020

(54) FUSION PROTEINS COMPRISING AN ALDOLASE ENZYME JOINED TO A MALTOSE BINDING PROTEIN

(71) Applicants: CONSEJO SUPERIOR DE INVESTIGACIONES CIENTÍFICAS, Madrid (ES); TECHNICAL UNIVERSITY OF DARMSTADT, Darmstadt (DE); SUSTAINABLE MOMENTUM, S.L., Las Palmas de Gran Canaria (ES)

(72) Inventors: Pedro Clapés Saborit, Barcelona (ES); Karel Hernández Sánchez, Barcelona (ES); Jesús Joglar Tamargo, Barcelona (ES); Jordi Bujons Vilás, Barcelona (ES); Wolf-Dieter Fessner, Darmstadt (DE); Pablo Domínguez De María, Las Palmas de Gran Canaria (ES)

(73) Assignees: CONSEJO SUPERIOR DE INVESTIGACIONES CIENTÍFICAS, Madrid (ES); TECHNICAL UNIVERSITY OF DARMSTADT, Darmstadt (DE); SUSTAINABLE MOMENTUM, S.L., Las Palmas de Gran Canaria (ES)

( * ) Notice: Subject to any disclaimer, the term of this patent is extended or adjusted under 35 U.S.C. 154(b) by 17 days.

(21) Appl. No.: 16/302,439

(22) PCT Filed: May 17, 2017

(86) PCT No.: PCT/EP2017/061850
§ 371 (c)(1),
(2) Date: Nov. 16, 2018

(87) PCT Pub. No.: WO2017/198717
PCT Pub. Date: Nov. 23, 2017

(65) Prior Publication Data
US 2019/0194638 A1 Jun. 27, 2019

(30) Foreign Application Priority Data
May 18, 2016 (EP) .................... 16382218

(51) Int. Cl.
*C12N 9/88* (2006.01)
*C12N 15/52* (2006.01)
*C12N 15/62* (2006.01)
*C12N 15/85* (2006.01)

(52) U.S. Cl.
CPC ............... *C12N 9/88* (2013.01); *C12N 15/52* (2013.01); *C12N 15/62* (2013.01); *C12N 15/85* (2013.01); *C07K 2319/24* (2013.01); *C12N 2015/8518* (2013.01); *C12Y 401/02* (2013.01)

(58) Field of Classification Search
None
See application file for complete search history.

(56) References Cited

FOREIGN PATENT DOCUMENTS

WO    2006/093322 A2    9/2006

OTHER PUBLICATIONS

Amarasinghe et al., "The Use of Affinity Tags to Overcome Obstacles in Recombinant Protein Expression and Purification," *Protein & Peptide Letters* 22:885-892, 2015.
Bae et al., "Cu/Zn Incorporation During Purification of Soluble Human EC-SOD from *E. coli* Stabilizes Proper Disulfide Bond Formation," *Appl. Biochem. Biotechnol.* 169:1633-1647, 2013. (16 pages).
GSP, "2,4-dihydroxyhept-2-ene-1,7-dioic acid aldolase yfaU SEQ ID No. 27.," Accession No. AEK20394, Jun. 15, 2007, URL=http://ibis.internal.epo.org/exam/dbfetch.jsp?id=GSP:AEK20394, download date Aug. 23, 2016, 1 page.
Huang et al., "Induced fit of passenger proteins fused to Archaea maltose binding proteins," *Biochemical and Biophysical Research Communications* 344:25-29, 2006. (6 pages).
Smyth et al., "Crystal structures of fusion proteins with large-affinity tags," *Protein Science* 12:1313-1322, 2003.
Tarpley et al., "Large-scale expression and purification of active pseudolysin in *Escherichia coli*," *The FASEB Journal* 27(1):Supplement 984.4, 2013. (1 page).
Terpe, "Overview of tag protein fusions: from molecular and biochemical fundamentals to commercial systems," *Appl. Microbiol. Biotechnol.* 60:523-533, 2003.
UniProt, "2-keto-3-deoxy-L-rhamnonate aldolase," Accession No. A0A0E0U178_ECOLX, Jul. 6, 2016, URL=http://ibis.internal.epo.org/exam/dbfetch.jsp?id=UNIPROT:A0A0E . . . , download date Aug. 24, 2016, 1 page.

*Primary Examiner* — Kagnew H Gebreyesus
(74) *Attorney, Agent, or Firm* — Seed IP Law Group LLP

(57) ABSTRACT

The present invention refers to an enzyme consisting of a fusion protein particularly useful as shown through-out the present invention for carrying out the carbon-carbon bond-forming reaction known as the aldol Reaction, preferably for carrying out an aldol reaction by using aldehydes as substrates and preferably pyruvate or a salt thereof, for producing hydroxyketoacids. Said enzyme is made by binding an aldolase to a maltose binding protein. The enzymes display full activity under "highly denaturing" substrate loadings (aldehydes, >1 M).

19 Claims, 2 Drawing Sheets
Specification includes a Sequence Listing.

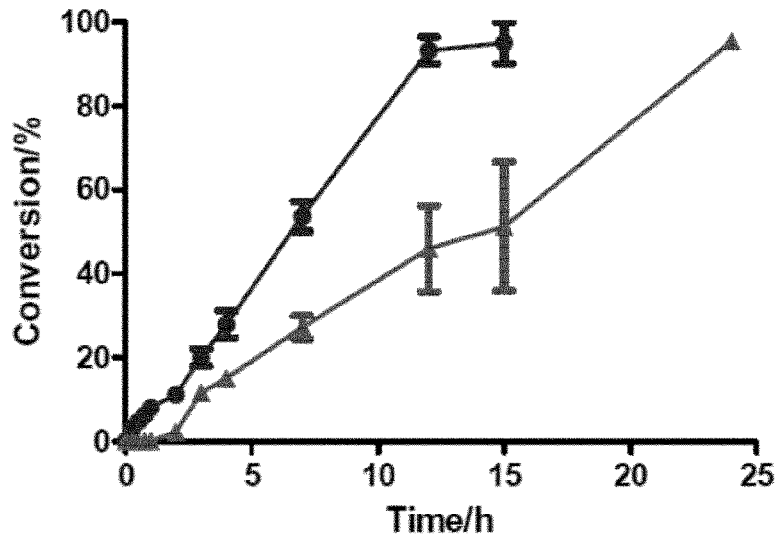

Fig. 3

MRGS<u>HHHHHH</u>GSG*IMKIEEGKLVIWINGDKGYNGLAEVGKKFEKDTGIKVTVEHPDKLEEKFPQVAATGDGPD IIFWAHDRFGGYAQSGLLAEITPDKAFQDKLYPFTWDAVRYNGKLIAYPIAVEALSLIYNKDLLPNPPKTWEEIPAL DKELKAKGKSALMFNLQEPYFTWPLIAADGGYAFKYENGKYDIKDVGVDNAGAKAGLTFLVDLIKNKHMNADT DYSIAEAAFNKGETAMTINGPWAWSNIDTSKVNYGVTVLPTFKGQPSKPFVGVLSAGINAASPNKELAKEFLENY LLTDEGLEAVNKDKPLGAVALKSYEEELAKDPRIAATMENAQKGEIMPNIPQMSAFWYAVRTAVINAASGRQT VDEALKDAQTSSG*<u>LEVLFQG</u>PACGTMNALLSNPFKERLRKGEVQIGLWLSSTTAYMAEIAATSGYDWLLIDGE HAPNTIQDLYHQLQAVAPYASQPVIRPVEGSKPLIKQVLDIGAQTLLIPMVDTAEQARQVVSATRYPPYGERG VGASVARAARWGRIENYMAQVNDSLCLLVQVESKTALDNLDEILDVEGIDGVFIGPADLSASLGYPDNAGHP EVQRIIETSIRRIRAAGKAAGFLAVAPDMAQQCLAWGANFVAVGVDTMLYSDALDQRLAMFKSGKNGPRIK GSY

Fig. 4

FUSION PROTEINS COMPRISING AN ALDOLASE ENZYME JOINED TO A MALTOSE BINDING PROTEIN

STATEMENT REGARDING SEQUENCE LISTING

The Sequence Listing associated with this application is provided in text format in lieu of a paper copy, and is hereby incorporated by reference into the specification. The name of the text file containing the Sequence Listing is 240242401USPC_SEQUENCE_LISTING.TXT. The text file is 56.4 KB, was created on Nov. 15, 2018, and is being submitted electronically via EFS-Web.

FIELD OF THE INVENTION

The present invention can be included in the field of chemistry, in particular in the field of enzymatic catalysis of aldol reactions.

BACKGROUND OF THE INVENTION

Industrial biocatalysis demands the set-up of bioprocesses with high substrate loadings, leading to high productivities in competitive reaction times. In this respect, the use of strong electrophilic reagents such as short-chain and highly reactive aldehydes typically leads to enzyme deactivation, thus decreasing the biocatalytic efficiency far from industrial requests.

In the realm of biocatalyis, C—C bond forming reactions represent a core strategy from which many valuable (optically active) building blocks and pharmaceutical precursors can be furnished. In this area, for example, hydroxyketoacids can be biocatalytically prepared by aldol addition of pyruvate to an aldehyde by a pyruvate-dependent aldolase. The hydroxyketoacid moiety can be found in a plethora of natural occurring important products such as sialic acids typically found in mammalian and bacterial glycoconjugates. A number of sialic acid derivatives have been prepared using biocatalytic approaches involving pyruvate-dependent aldolases catalyzing the aldol addition of pyruvate to analogues and derivatives of N-acetyl-mannosamine. In this area, class I pyruvate-dependent aldolases are normally used with rather strict selectivity for the donor substrate (i.e. pyruvate) but with a fairly broad tolerance of acceptor substrates such as a number of sugars and their derivatives larger or equal to pentoses. However, small open-chain aldehydes such as glyceraldehyde, glycolaldehyde, aliphatic, aromatic aldehyde are not acceptable. Likewise, the inherent high reactivity of those aldehydes tends to deactivate the enzymes (especially when used at high substrate loadings), making the processes often inefficient from an economic viewpoint.

Given the potential of lyases and C—C bond forming reactions for industrial purposes, and the aforementioned challenges found in the prior art, what is needed is the set-up of biocatalytic processes comprising enzymes that may be largely stable and active under very high substrate loadings, leading to robust industrial bioprocesses.

BRIEF DESCRIPTION OF THE INVENTION

The present invention solves the above problem by providing those Class I and Class II aldolases that utilize pyruvate or other α-ketoacid derivatives as nucleophilic components in aldol reactions expressed as fusion proteins with the maltose binding protein (MBP) (see the examples for an explanation of a non-limiting manner of manufacturing or producing the aforesaid fusion proteins). Preferably, said aldolase is a 2-keto-3-deoxy-L-rhamnonate aldolase or a variant thereof. Also preferably, said maltose binding protein is a variant thereof.

Such fusion proteins as defined above are particularly useful, as shown through-out the present invention, for carrying out the carbon-carbon bond-forming reaction known as the aldol reaction, preferably for carrying out an aldol reaction for producing hydroxyketoacids by using as substrates aldehydes and α-ketoacids, preferably pyruvate or a salt thereof, preferably at high substrate loadings.

BRIEF DESCRIPTION OF THE FIGURES

FIG. 3. Reaction kinetics of aldol addition of pyruvate (1.7 M) to formaldehyde (1.7 M) in sodium phosphate buffer (50 mM pH 7.0) in the presence of either $Ni^{2+}$ (●) or $Co^{2+}$ (▲).

FIG. 4. Sequence of fused maltose binding protein (MBP) and 2-keto-3-deoxy-L-rhamnonate aldolase (YfaU) (MPB-YfaU). MBP (italic), YfaU (bold), 6×His tag (underlined) and recognition and cleavage site for human rhinovirus 3C and PreScission proteases (bold and underlined).

DETAILED DESCRIPTION OF THE INVENTION

Definitions

Figure 1:
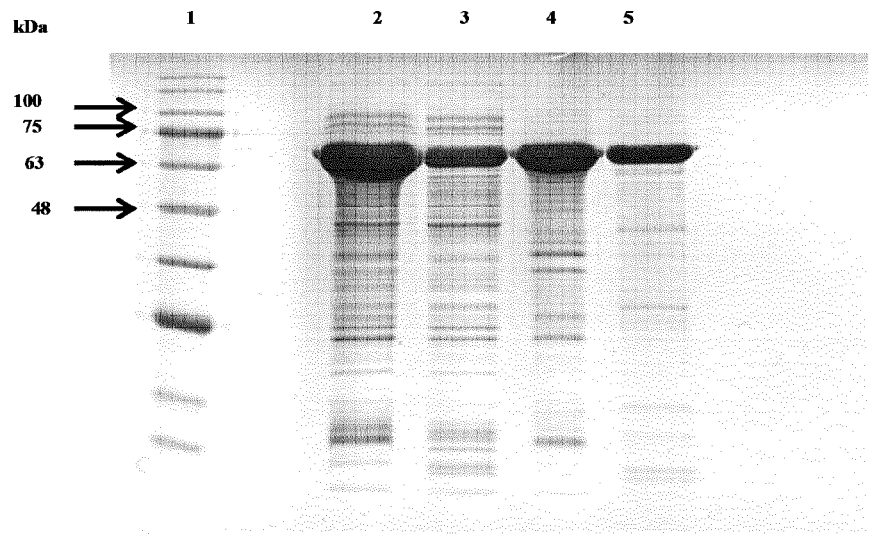
FIG. 1. Coomassie Blue-stained SDS-PAGE of purified MBP-YfaU. The gel was loaded with sample of MPB-YfaU from crude extract (lane 2), supernatant of lysis (lane 3), pellet after lysis and centrifugation (lane 4), and eluate of affinity chromatography (IMAC) (lane 5). The molecular masses of the proteins in the standard (lane 1) are indicated beside the gel. The predicted molecular mass of MBP-YfaU is 72 kDa.

"Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used.

In the context of the present invention, the term "aldolase" is understood as any class of enzyme that reversibly catalyzes the cleavage of carbon-carbon bonds.

As used herein, the term "Class II aldolase" is understood as established according to the classification scheme that divides aldolases into Class I and Class II as developed by Marsh and Lebherz 1992.

As used herein, the term "Class II pyruvate-dependent aldolase enzyme" is understood as an aldolase that needs a divalent metal cofactor to be catalytically active and utilize pyruvate or other α-ketoacid derivatives as nucleophilic components in aldol reactions.

As used herein, the term "2-keto-3-deoxy-L-rhamnonate aldolase or YfaU" is understood as a Class II pyruvate-dependent aldolase enzyme having amino acid sequence SEQ ID No 1.

In the context of the present invention, the term "fusion protein" is understood as a protein made from a fusion gene, which is created by joining complete or parts of two or more individual genes that originally coded for separate proteins linked or not through a peptide spacer sequence. Fusion genes may occur naturally in the body by transfer of DNA between chromosomes. Fusion genes and proteins can also be made in the laboratory by combining genes or parts of genes from the same or different organisms. Translation of this fusion gene results in a single or multiple polypeptides with functional properties derived from each of the original proteins.

As used herein, the term "fusion gene" is understood as a gene made by joining complete or parts of two or more individual genes that originally coded for separate proteins linked or not through a peptide spacer sequence. Fusion genes can be made in the laboratory by combining genes or parts of genes from the same or different organisms.

In the context of the present invention, SED ID NO 2 is understood as a gene sequence (gi|388476123:c2363515-2362712 *Escherichia coli* str. K-12 substr. W3110, complete genome).

```
Gene sequence
                                            (SEQ ID NO 2)
ATGAACGCATTATTAAGCAATCCCTTTAAAGAACGTTTACGCAAGGGCG

AAGTGCAAATTGGTCTGTGGTTAAGCTCAACGACTGCCTATATGGCAGA

AATTGCCGCCACTTCTGGTTATGACTGGTTGCTGATTGACGGGGAGCAC

GCGCCAAACACCATTCAGGATCTTTATCATCAGCTACAGGCGGTAGCGC

CCTATGCCAGCCAACCCGTGATCCGTCCGGTGGAAGGCAGTAAACCGCT

GATTAAACAAGTCCTGGATATTGGCGCGCAAACTCTACTGATCCCGATG

GTCGATACTGCCGAACAGGCACGTCAGGTGGTGTCTGCCACGCGCTATC

CTCCCTACGGTGAGCGTGGTGTCGGGGCCAGTGTGGCACGGGCTGCGCG

CTGGGGACGCATTGAGAATTACATGGCGCAAGTTAACGATTCGCTTTGT

CTGTTGGTGCAGGTGGAAAGTAAAACGGCACTGGATAACCTGGACGAAA

TCCTCGACGTCGAAGGGATTGATGGCGTGTTTATTGGACCTGCGGATCT

TTCTGCGTCGTTGGGCTACCCGGATAACGCCGGGCACCCGGAAGTGCAG
```

-continued
```
CGAATTATTGAAACCAGTATTCGGCGGATCCGTGCTGCGGGTAAAGCGG

CTGGTTTTCTGGCTGTGGCTCCTGATATGGCGCAGCAATGCCTGGCGTG

GGGAGCGAACTTTGTCGCTGTTGGCGTTGACACGATGCTCTACAGCGAT

GCCCTGGATCAACGACTGGCGATGTTTAAATCAGGCAAAAATGGGCCAC

GCATAAAAGGTAGTTATTGA
```

In the context of the present invention, SEQ ID NO 1 is understood as the protein sequence of YfaU (EC 4.1.2.53, 2-keto-3-deoxy-L-rhamnonate aldolase) (P76469|2-keto-3-deoxy-L-rhamnonate aldolase |EC 4.1.2.53| *Escherichia coli* (strain K12)|Swiss-Prot.

```
Protein sequence
                                            (SEQ ID NO 1)
MNALLSNPFKERLRKGEVQIGLWLSSTTAYMAEIAATSGYDWLLIDGEH

APNTIQDLYHQLQAVAPYASQPVIRPVEGSKPLIKQVLDIGAQTLLIPM

VDTAEQARQVVSATRYPPYGERGVGASVARAARWGRIENYMAQVNDSLC

LLVQVESKTALDNLDEILDVEGIDGVFIGPADLSASLGYPDNAGHPEVQ

RIIETSIRRIRAAGKAAGFLAVAPDMAQQCLAWGANFVAVGVDTMLYSD

ALDQRLAMFKSGKNGPRIKGSY
```

As used herein, variants of YfaU refer to amino acid sequences exhibiting 2-keto-3-deoxy-L-rhamnonate aldolase activity. Preferably, as used herein variants of YfaU refer to amino acid sequences exhibiting 2-keto-3-deoxy-L-rhamnonate aldolase activity and having at least 80%, and most preferably 85%, 90%, 95%, 96%, 97%, 98% or 99% sequence identity with amino acid sequence SEQ ID NO 1 or with an amino acid sequence coded by SEQ ID NO 2.

As used herein "Maltose binding proteins or MBP" refer to periplasmic proteins that bind maltose and maltodextrin, take part in the maltose transport system of bacteria and are used to increase the solubility of recombinant proteins expressed in bacteria such as *E. coli* preventing aggregation of the protein of interest. In particular, "Maltose binding protein or MBP" refers to protein sequence SEQ ID NO 8:

```
MKIEEGKLVIWINGDKGYNGLAEVGKKFEKDTGIKVTVEHPDKLEEKFP

QVAATGDGPDIIFWAHDRFGGYAQSGLLAEITPDKAFQDKLYPFTWDAV

RYNGKLIAYPIAVEALSLIYNKDLLPNPPKTWEEIPALDKELKAKGKSA

LMFNLQEPYFTWPLIAADGGYAFKYENGKYDIKDVGVDNAGAKAGLTFL

VDLIKNKHMNADTDYSIAEAAFNKGETAMTINGPWAWSNIDTSKVNYGV

TVLPTFKGQPSKPFVGVLSAGINAASPNKELAKEFLENYLLTDEGLEAV

NKDKPLGAVALKSYEEELAKDPRIAATMENAQKGEIMPNIPQMSAFWYA

VRTAVINAASGRQTVDEALKDAQT
```

As used herein, variants of MBP refer to amino acid sequences exhibiting at least 80%, 85%, 90%, 95%, 96%, 97%, 98% or 99% sequence identity with amino acid sequence SEQ ID NO 8 capable of increasing the solubility of recombinant proteins expressed in bacteriae such as *E. coli* and preventing aggregation of the protein of interest.

As used herein the term "MBP-YfaU" refers to the fusion protein comprising YfaU or a variant thereof bound to the maltose binding protein (MBP) or a variant thereof. It is noted that the term "variant" as used herein only specifically refers to the protein sequences MBP or YfaU and not to any additional sequence of the fusion protein. Preferably, MBP-YfaU comprises the amino acid sequence reproduced herein (SEQ ID NO 9):

MKIEEGKLVIWINGDKGYNGLAEVGKKFEKDTGIKVTVEHPDKLEEKFP

QVAATGDGPDIIFWAHDRFGGYAQSGLLAEITPDKAFQDKLYPFTWDAV

RYNGKLIAYPIAVEALSLIYNKDLLPNPPKTWEEIPALDKELKAKGKSA

LMFNLQEPYFTWPLIAADGGYAFKYENGKYDIKDVGVDNAGAKAGLTFL

VDLIKNKHMNADTDYSIAEAAFNKGETAMTINGPWAWSNIDTSKVNYGV

TVLPTFKGQPSKPFVGVLSAGINAASPNKELAKEFLENYLLTDEGLEAV

NKDKPLGAVALKSYEEELAKDPRIAATMENAQKGEIMPNIPQMSAFWYA

VRTAVINAASGRQTVDEALKDAQT<u>SSGLEVLFQGPACGT</u>MNALLSNPFK

ERLRKGEVQIGLWLSSTTAYMAEIAATSGYDWLLIDGEHAPNTIQDLYH

QLQAVAPYASQPVIRPVEGSKPLIKQVLDIGAQTLLIPMVDTAEQARQV

VSATRYPPYGERGVGASVARAARWGRIENYMAQVNDSLCLLVQVESKTA

LDNLDEILDVEGIDGVFIGPADLSASLGYPDNAGHPEVQRIIETSIRRI

RAAGKAAGFLAVAPDMAQQCLAWGANFVAVGVDTMLYSDALDQRLAMFK

SGKNGPRIKGSY wherein the peptide sequence SSGLEVLFQGPACGT (outlined above) is understood as a "peptide linker" or "spacer sequence" and can be replaced by any suitable linker as establish in the definition below. In addition it is further noted that the above sequence can further comprise any vector suitable for affinity protein purification as for example, but not limited to, a N-terminal (His)6-tag peptide sequence.

Preferably, MBP-YfaU comprises the amino acid sequence shown in FIG. 4, which is also reproduced herein (SEQ ID NO 10):

MRGSHHHHHHGSGIMKIEEGKLVIWINGDKGYNGLAEVGKKFEKDTGIK

VTVEHPDKLEEKFPQVAATGDGPDIIFWAHDRFGGYAQSGLLAEITPDK

AFQDKLYPFTWDAVRYNGKLIAYPIAVEALSLIYNKDLLPNPPKTWEEI

PALDKELKAKGKSALMFNLQEPYFTWPLIAADGGYAFKYENGKYDIKDV

GVDNAGAKAGLTFLVDLIKNKHMNADTDYSIAEAAFNKGETAMTINGPW

AWSNIDTSKVNYGVTVLPTFKGQPSKPFVGVLSAGINAASPNKELAKEF

LENYLLTDEGLEAVNKDKPLGAVALKSYEEELAKDPRIAATMENAQKGE

IMPNIPQMSAFWYAVRTAVINAASGRQTVDEALKDAQTSSGLEVLFQGP

ACGTMNALLSNPFKERLRKGEVQIGLWLSSTTAYMAEIAATSGYDWLLI

DGEHAPNTIQDLYHQLQAVAPYASQPVIRPVEGSKPLIKQVLDIGAQTL

LIPMVDTAEQARQVVSATRYPPYGERGVGASVARAARWGRIENYMAQVN

DSLCLLVQVESKTALDNLDEILDVEGIDGVFIGPADLSASLGYPDNAGH

PEVQRIIETSIRRIRAAGKAAGFLAVAPDMAQQCLAWGANFVAVGVDTM

LYSDALDQRLAMFKSGKNGPRIKGSY

As used herein, the term "bound to" as referred to the fusion protein of the present invention is understood as protein linked to another protein directly or through a peptide spacer sequence.

It is noted that linkers or spacer sequences are usually short peptide sequences that occur between protein domains. Linkers are often composed of flexible residues like glycine and serine so that the adjacent protein domains are free to move relative to one another. Longer linkers are used when it is necessary to ensure that two adjacent domains do not sterically interfere with one another. In particular, as used herein, the term "peptide linker" or "spacer sequence" refers to amino acid sequences of essentially any length (e.g., 2, 3, 4, 5, 6, 7, 8, 9, 10, 11, 12, 13, 14, 15, 16, 17, 18, 19, 20, or more amino acids) between the MBP or any variant thereof and the YfaU or any variant thereof having or consisting of preferably from 2 to 100 amino acids, preferably from 3 to 50 amino acids, more preferably from 3 to 40 amino acids, more preferably from 10 to 30 amino acids, more preferably having or consisting of about 15 amino acids. The selection of a linker sequence and length is dependent on the construction of functional chimeric proteins, and therefore, the optimal linker length will vary on a case by case basis. Anyhow, the incorporation of linkers for the construction of stable and bioactive recombinant fusion proteins is well known in the state of the art as shown i.e in Xiaoying Chen et al. Fusion Protein Linkers: Property, Design and Functionality. Adv Drug Deliv Rev. 2013, 65(10): 1357-1369 or in Vishnu Priyanka et al. Linkers in the structural biology of protein-protein interactions. Protein Sci. 2013, 22(2): 153-167.

As used herein "YfaU W23V" refers to the protein sequence SEQ ID NO 3:

MNALLSNPFKERLRKGEVQIGLVLSSTTAYMAEIAATSGYDWLLIDGEH

APNTIQDLYHQLQAVAPYASQPVIRPVEGSKPLIKQVLDIGAQTLLIPM

VDTAEQARQVVSATRYPPYGERGVGASVARAARWGRIENYMAQVNDSLC

LLVQVESKTALDNLDEILDVEGIDGVFIGPADLSASLGYPDNAGHPEVQ

RIIETSIRRIRAAGKAAGFLAVAPDMAQQCLAWGANFVAVGVDTMLYSD

ALDQRLAMFKSGKNGPRIKGSY

As used herein "YfaU L216A" refers to the protein sequence SEQ ID NO 4:

MNALLSNPFKERLRKGEVQIGLWLSSTTAYMAEIAATSGYDWLLIDGEH

APNTIQDLYHQLQAVAPYASQPVIRPVEGSKPLIKQVLDIGAQTLLIPM

VDTAEQARQVVSATRYPPYGERGVGASVARAARWGRIENYMAQVNDSLC

LLVQVESKTALDNLDEILDVEGIDGVFIGPADLSASLGYPDNAGHPEVQ

RIIETSIRRIRAAGKAAGFAAVAPDMAQQCLAWGANFVAVGVDTMLYSD

ALDQRLAMFKSGKNGPRIKGSY

As used herein "YfaU W23V L216A" refers to the protein sequence SEQ ID NO 5:

MNALLSNPFKERLRKGEVQIGLVLSSTTAYMAEIAATSGYDWLLIDGEH

APNTIQDLYHQLQAVAPYASQPVIRPVEGSKPLIKQVLDIGAQTLLIPM

VDTAEQARQVVSATRYPPYGERGVGASVARAARWGRIENYMAQVNDSLC

-continued

```
LLVQVESKTALDNLDEILDVEGIDGVFIGPADLSASLGYPDNAGHPEVQ
RIIETSIRRIRAAGKAAGFAAVAPDMAQQCLAWGANFVAVGVDTMLYSD
ALDQRLAMFKSGKNGPRIKGSY
```

As used herein "YfaU W23V F174V L216A" refers to the protein sequence SEQ ID NO 6:

```
MNALLSNPFKERLRKGEVQIGLVLSSTTAYMAEIAATSGYDWLLIDGEH
APNTIQDLYHQLQAVAPYASQPVIRPVEGSKPLIKQVLDIGAQTLLIPM
VDTAEQARQVVSATRYPPYGERGVGASVARAARWGRIENYMAQVNDSLC
LLVQVESKTALDNLDEILDVEGIDGVVIGPADLSASLGYPDNAGHPEVQ
RIIETSIRRIRAAGKAAGFAAVAPDMAQQCLAWGANFVAVGVDTMLYSD
ALDQRLAMFKSGKNGPRIKGSY
```

As used herein "YfaU W23A L216A" refers to the protein sequence SEQ ID NO 7:

```
MNALLSNPFKERLRKGEVQIGLALSSTTAYMAEIAATSGYDWLLIDGEH
APNTIQDLYHQLQAVAPYASQPVIRPVEGSKPLIKQVLDIGAQTLLIPM
VDTAEQARQVVSATRYPPYGERGVGASVARAARWGRIENYMAQVNDSLC
LLVQVESKTALDNLDEILDVEGIDGVFIGPADLSASLGYPDNAGHPEVQ
RIIETSIRRIRAAGKAAGFAAVAPDMAQQCLAWGANFVAVGVDTMLYSD
ALDQRLAMFKSGKNGPRIKGSY
```

As used herein MBP-YfaU being YfaU any of its variants, is preferably understood as YfaU W23V, YfaU L216A, YfaU W23V L216A, YfaU W23V F174V L216A and YfaU W23A L216A bound to, directly or through a peptide spacer sequence, to the MBP as defined above.

The term "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

Description

In the present invention, MBP-YfaU enzyme is successfully used to synthesize L-homoserine through two enzymatic consecutive reactions (Scheme 1).

Scheme 1.

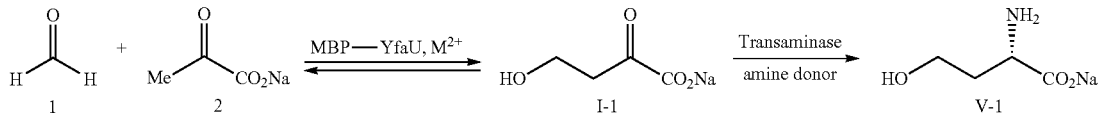

Reaction scheme for the synthesis of L-homoserine (V-1). Aldol addition of pyruvate (2) to formaldehyde (1) catalyzed by MBP-YfaU from E. coli K12 and an (S)-selective transaminase -catalyzed reaction between an amino donor and I-1.

The first reaction is the aldol addition of pyruvate (2) to formaldehyde (1) using a pyruvate aldolase (Scheme 1). The second step comprises a transamination reaction using 4-hydroxy-2-oxobutanoic acid (I-1), the aldol adduct obtained in the first step, to obtain L-homoserine (V-1) a compound with high industrial relevance and interest.

For the first step (carboligation), the metal-dependent Class II pyruvate aldolase 2-keto-3-deoxy-L-rhamnonate aldolase (YfaU, EC 4.1.2.53) from E. coli K12 was assessed. However, it was found that the wild-type enzyme was expressed mainly as inclusion bodies and thus a priori useless as a biocatalyst. To overcome this limitation the enzyme was expressed as a fusion protein with different proteins which, a priori, were capable of increasing the solubility of recombinant proteins expressed in bacteriae such as E. coli and preventing aggregation of the protein of interest. In this sense, the enzyme was expressed as a fusion protein with dihydrofolate reductase (DHFR, insert in commercial pQE40), d-fructose-6-phosphate aldolase (FSA) from E. coli and NusA protein from E. coli and with maltose binding protein (MBP). DHFR-YfaU and FSA-YfaU were expressed as inclusion bodies and only NusA-YfaU and MBP-YfaU were soluble. Even soluble, NusA-YfaU showed an activity 14-fold lower than MBP-YfaU. MBP-YfaU was expressed efficiently with good protein solubility and also catalyzed the reaction successfully. Although DHFR, MBP and NusA are known to enhance the solubility of proteins that are expressed as inclusion bodies, the final activity depends on the substrate. Hence, there is no direct correlation between solubility and enzymatic activity.

Figure 2:
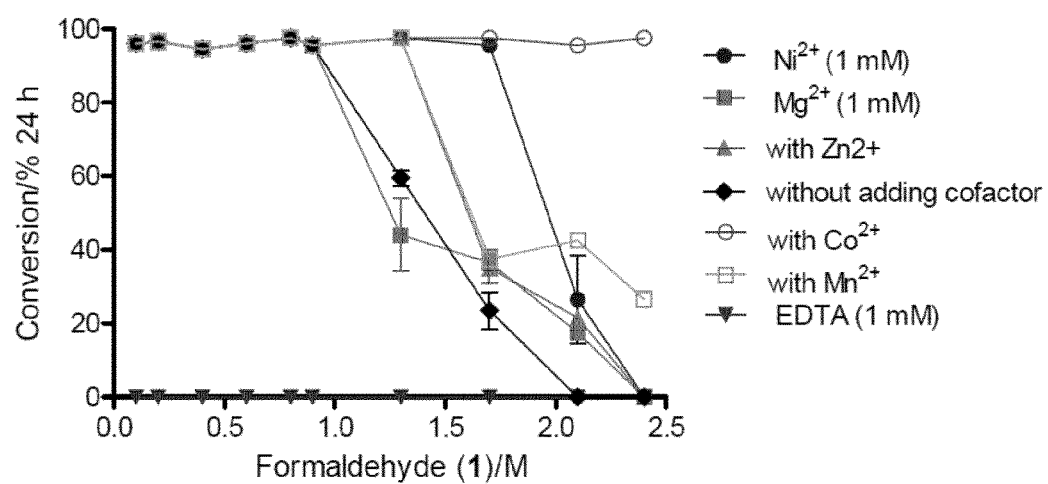
FIG. 2. Aldol addition of pyruvate (1) to formaldehyde (2) in sodium phosphate buffer (50 mM, pH 7.0) at 24 h of reaction using equal molar ratio of reactants. The influence of formaldehyde concentration and metal cofactor was studied: $Ni^{2+}$ (●), $Mg^{2+}$ (■), $Zn^{2+}$ (▲), $Co^{2+}$ (○), $Mn^{2+}$ (□), without adding metal (♦) and with EDTA (▼).

In addition, quite remarkably, by using MBP-YfaU the enzyme resulted fully active even at extremely high concentrations of formaldehyde and pyruvate (>1 M). This is surprising, as highly electrophilic aldehydes such as formaldehyde are known to be strong denaturing agents for enzymes. Furthermore, the addition of some divalent metals led surprisingly to even higher stabilities and substrate conversions (up to 2.5 M). A summary of these experiments is depicted in FIG. 2.

The best results were achieved at formaldehyde and pyruvate concentrations of >1.7 M, and using $Co^{2+}$ or $Ni^{2+}$ as alternative metal cofactors (1 mM the minimum concentration to effectively exchange the naturally occurring cofactor, $Mg^{2+}$, in the active site). Under these "denaturing" conditions, virtually full conversion was achieved, leading to a I-1 productivity of >197 g $L^{-1}$ $d^{-1}$.

Studies on kinetics were further assessed, at 1.7 M concentrations of both substrates and using either $Co^{2+}$ or $Ni^{2+}$ as metals (1 mM). Results are depicted in FIG. 3. According to these results, the addition of $Ni^{2+}$ led to a significantly higher reaction rate compared to $Co^{2+}$ when using each 1.7 M of formaldehyde and pyruvate (FIG. 3).

Consequently, the present invention, has surprisingly found that:

i) The MBP-YfaU enzyme catalyzed the reactions, as confirmed by different blank reaction procedures such as no enzyme addition, use of BSA protein with $Ni^{2+}$ or $Co^{2+}$ addition or use of EDTA to remove metals, which led to no conversion or insignificant background condensation of less than 0.5% in 24 h.

ii) MBP-YfaU resulted fully active even at extremely high concentrations of formaldehyde and pyruvate (>1 M). Furthermore, the addition of some divalent metals (e.g. $Co^{2+}$, $Ni^{2+}$, $Mn^{2+}$) led surprisingly to even higher stabilities and substrate conversions (up to 2.5 M).

iii) The best results were achieved at formaldehyde and pyruvate concentrations of >1.7 M, and using $Co^{2+}$ or $Ni^{2+}$ (1 mM). Under these conditions, virtually full conversion was achieved, leading to a productivity of >197 g $L^{-1}$ $d^{-1}$, which is remarkably high and attractive for industrial applications.

iv) Under certain conditions (example 5) a subsequent addition of the primary aldol adduct to a second equivalent of formaldehyde, thereinafter double addition, was observed providing advantages in two directions. On one hand, the selectivity towards the desired mono-addition product can be easily modulated by changing reaction conditions. For instance, by using $Mg^{2+}$ and slow addition of formaldehyde up to 1 M, product I-1 was isolated in 89% yield. On the other hand, innovative products or intermediates can be easily accessible. For instance preparation of sodium 4-hydroxy-3-(hydroxymethyl)-2-oxobutanoate (1-5, example 5).

v) YfaU has the ability to control aldol addition stereochemistry. The configuration of the new generated stereogenic centers depends on the enzyme and on the aldol addition reagents.

Therefore, as illustrated above and in the examples of the present invention, the MBP-YfaU enzyme has a clear potential for its use in industrial bio-transformations, in particular for the synthesis of L-homoserine, when multi-step processes are envisaged.

It is particularly noted that variants of the MBP-YfaU enzyme can be used in the above identified processes such as YfaU W23V, YfaU L216A, YfaU W23V L216A, YfaU W23V F174V L216A and YfaU W23A L216A (see "definitions" above), although *E. coli* K12 YfaU with SEQ ID NO1 is particularly preferred. The metal-dependent Class II pyruvate-dependent aldolase 2-keto-3-deoxy-L-rhamnonate aldolase (YfaU, EC 4.1.2.53) from *E. coli* K12 as used in the present invention, was expressed in *E. coli* M-15 strain, derived from *E. coli* K-12 strain and subsequently purified. The enzyme referred to herein above as the preferred YfaU enzyme is the wild type form of the enzyme, which naturally occurs in *E. coli* K12 with an amino acid sequence corresponding to SEQ ID NO 1. However, as already stated, variants of this enzyme capable of carrying out the reaction as stablished in scheme 1 above and that at the same time exhibit at least 80%, 85%, 90%, and most preferably at least 95%, 96%, 97%, 98% or 99% sequence identity with amino acid sequence SEQ ID NO 1 or with an amino acid sequence coded by SEQ ID NO 2 are also suitable to carry out the present invention as fusion proteins with MBP. Moreover, other wild type YfaU enzymes can be isolated and identified in other microorganisms due to the information and processes existing in the state of the art. Therefore, other Class I and/or Class II aldolases that utilize pyruvate or other ketoacid derivatives as nucleophilic components in aldol reactions, preferably Class II pyruvate-dependent aldolase enzymes, apart from YfaU, are also suitable to carry out the present invention.

Therefore, a first aspect of the invention refers to Class I and/or Class II aldolases that utilize pyruvate or other ketoacid derivatives as nucleophilic components in aldol reactions, preferably to a Class II pyruvate-dependent aldolase enzyme, expressed as a fusion protein with the maltose binding protein (MBP) (see the examples for an explanation of a non-limiting manner of manufacturing or producing the aforesaid fusion protein). Preferably, said Class II pyruvate-dependent aldolase is a 2-keto-3-deoxy-L-rhamnonate aldolase or a variant thereof. Most preferably the fusion protein is MBP-YfaU, wherein MBP or YfaU can also include variants of any of these proteins.

Examples of preferred YfaU variant sequences are SEQ ID NO 3 (YfaU W23V), SEQ ID NO 4 (YfaU L216A), SEQ ID NO 5 (YfaU W23V L216A), SEQ ID NO 6 (YfaU W23V F174V L216A) and SEQ ID NO 7 (YfaU W23A L216A).

Also preferably, said maltose binding protein corresponds to a protein having SEQ ID NO 8 or a variant thereof.

The aforesaid fusion proteins thus comprise, consist essentially of or consist preferably of a Class II pyruvate-dependent aldolase enzyme and a maltose binding protein, wherein these two proteins are bound to each other either directly or by a peptide linker as defined in the section entitled "definitions" above, preferably said linker having from 2 to 100 amino acids, preferably from 3 to 50 amino acids, more preferably from 3 to 40 amino acids, more preferably from 10 to 30 amino acids, more preferably having about 15 amino acids in length.

A preferred embodiment of the first aspect of the invention refers to a composition comprising the fusion protein as defined in the first aspect of the invention which may optionally further comprise divalent metals, preferably $Mg^{2+}$, $Co^{2+}$ and/or $Ni^{2+}$. +. It is in addition noted that, the fusion protein, optionally comprising divalent metals, preferably $Mg^{2+}$, $Co^{2+}$ and/or $Ni^{2+}$, can be combined and dialyzed against different buffers, being phosphate and 3-(N-morpholino)propanesulfonate (MOPS) buffers preferred.

It is noted that the fusion protein of the present invention can be lyophilized or freezed and thus the composition referred to herein can be found, for example, as a lyophilized powder composition.

It is further noted that the composition referred to in the first aspect of the invention or in any of its preferred embodiments, can further comprise additional enzymes such as reductases, decarboxylases or transaminases such as transaminase Prozomix TA051, TA039 or TA026 for L-derivatives and Prozomix TA07, TA017 or TA043 for D-derivatives (preferably a lyophilized crude cell free extract). Finally, the fusion protein of the present invention may be also used as immobilized enzyme, or within a whole-cell to enable even more robust biocatalytic industrial processes, or in any other form that skilled-in-the-art may envisage.

A second aspect of the invention refers to a fusion gene or polynucleotide coding for the fusion protein as defined in the first aspect of the invention.

A third aspect of the invention refers to a plasmid or vector, preferably a viral or non-viral vector, comprising the fusion gene as defined in the second aspect of the invention.

A fourth aspect of the invention refers to a prokaryotic or eukaryotic microorganism such as a cell, preferably a prokaryotic cell, more preferably a bacterial strain such as *E. coli*, or also preferably an eukaryotic microorganism such as a yeast (preferably comprising a signal peptide useful for secretion of heterologous proteins), modified, transformed, transduced or transfected with the fusion gene of the second aspect of the invention. Preferably, said prokaryotic or eukaryotic cell is capable of expressing the fusion protein as defined in the first aspect of the invention.

A fifth aspect of the invention refers to a method for producing the fusion protein as defined in the first aspect of the invention comprising the expression of said protein by using the prokaryotic or eukaryotic cell as defined in the fourth aspect of the invention. A preferred embodiment of the fifth aspect of the invention refers to a process or method of producing 2-keto-3-deoxy-L-rhamnonate aldolase or a variant thereof as defined above, expressed as a fusion protein with a maltose binding protein (MBP) or a variant thereof, which comprises expressing said protein by using a modified microorganism as defined in the fourth aspect above, such as a bacterial strain (i.e. *E. coli*) or a yeast, with the fusion gene coding for the aforesaid fusion protein as defined in the second aspect of the invention.

A sixth aspect of the invention refers to a fusion protein obtained or obtainable by the method of the fifth aspect of the invention.

A seventh aspect of the invention refers to the use of the fusion protein as defined in the first aspect of the invention for carrying out the carbon-carbon bond-forming reaction known as the Aldol Reaction, preferably for carrying out an aldol reaction by using aldehydes as substrates and an α-ketoacid, preferably pyruvate or a salt thereof, preferably for producing hydroxyketoacids, and preferably at "high denaturing" substrate loadings.

A preferred embodiment of the seventh aspect of the invention refers to the use of the fusion protein as defined in the first aspect of the invention or to the composition as defined in the first aspect of the invention for the preparation of hydroxyketoacids of formula I,

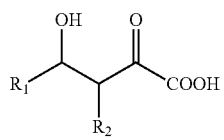

I or any stereoisomers and mixtures thereof, or any salts or solvates thereof, wherein $R_1$ is selected from —H, —($C_1$-$C_6$)alkyl, —($C_0$-$C_3$)alkylaryl, —$(CH_2)_m OCH_2$aryl, wherein m is an integer number from 1 to 6, and substituents of formula II, III or IV:

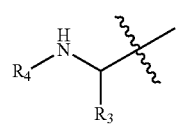

II

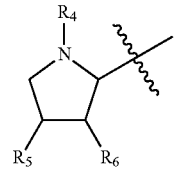

III

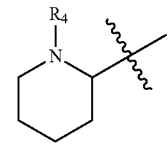

IV $R_2$ is selected from —H, —OH and —($C_1$-$C_6$)alkyl;
$R_3$ is selected from —H, —($C_1$-$C_8$)alkyl, and —($C_0$-$C_3$)alkylaryl;
$R_4$ is selected from —H and PG, wherein PG is a protecting group selected from benzyloxycarbonyl (Cbz), tert-butyloxycarbonyl (Boc), phenylacetyl (PheAc), fluoren-9-ylmethoxycarbonyl (Fmoc), acetyl (Ac), benzyl (Bn), and benzoyl (Bz);
$R_5$ and $R_6$ are selected independently from —H, —OH and —($C_1$-$C_3$)alkyl; and wherein the alkyl and aryl moieties in $R_1$, $R_2$ and $R_3$ are optionally substituted with one or two groups selected independently from halogen, —OR, —NHR, —NRR' being R and R' selected from —H and —($C_1$-$C_3$)alkyl.

As used herein the term "($C_1$-$C_6$)alkyl" relates to a radical derived from a monovalent alkane (hydrocarbon), of linear or branched chain, containing from one to six carbon atoms and includes groups such as methyl, ethyl, propyl, isopropyl, butyl, isobutyl, sec-butyl or tert-butyl. Similarly, the term "($C_1$-$C_8$)alkyl" is used in this specification to refer to alkyl groups of 1 to 8 carbon atoms. Alkyl groups may be optionally substituted by one or two groups such as halogen, hydroxyl, alkoxy and amino.

As used herein the term "aryl", alone or in combination, refers to a system of mono- or polycyclic aromatic ring containing carbon ring atoms. Preferred aryl ring systems are 5-10 monocyclic or bicyclical members, such as phenyl or biphenyl, which optionally carry one or two groups such as halogen, hydroxyl, alkoxy and amino.

The compounds of the present invention may have acid protons and, therefore they may form salts with bases. Examples of these salts include salts with metal cations, such as for example an alkaline metal ion, an alkaline-earth metal ion or an aluminium ion. Likewise, the compounds of the present invention may contain a basic nitrogen and they may form salts with acid. Examples of salts include among others inorganic acids, such as hydrochloric, hydrobromic, hydroioidic, nitric, sulphuric, phosphoric as well as organic acids as acetic, trifluorometansulfonic, etc. Some of the compounds of the invention may exist as unsolvated as well as solvated forms such as, for example, hydrates or alcohol solvates.

Many of the organic compounds mentioned herein exist in optically active forms having the ability to rotate the plane of plane-polarized light. In describing an optically active compound, the prefixes D and L or R and S are used to denote the absolute configuration of the molecule about its chiral center(s). The prefixes D and L or (+) and (−) are employed to designate the sign of rotation of plane-polarized light by the compound, with (−) or L meaning that the compound is levorotatory. A compound prefixed with (+) or D is dextrorotatory. Compounds of formula I of the present invention may comprise one or more chiral centers. The present invention includes each one of the possible stereoisomers and mixtures thereof, particularly racemic mixtures thereof. Some of the compounds of the present invention may exist as enantiomers or as several diastereoisomers. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Certain materials, compounds, compositions, and components disclosed herein can be obtained commercially or readily synthesized using techniques generally known to those skilled in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Another preferred embodiment of the seventh aspect of the invention refers to the use of compounds of formula I obtained by using the method of the invention as intermediates for the preparation of compounds of formula V

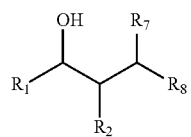

V or any stereoisomers and mixtures thereof, or any salts or solvates thereof,
wherein
$R_1$ is selected from —H, —($C_1$-$C_6$)alkyl, —($C_0$-$C_3$)alkylaryl, $(CH_2)_m OCH_2$aryl, wherein m is an integer number from 1 to 6, and substituents of formula II, III or IV

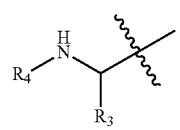

II

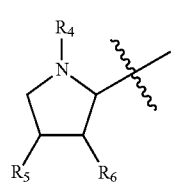

III

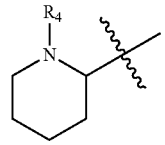

IV $R_2$ is selected from —H, —OH, and —($C_1$-$C_6$)alkyl;
$R_3$ is selected from —H, —($C_1$-$C_8$)alkyl, and a —($C_0$-$C_3$)alkylaryl;
$R_4$ is selected from —H and PG, wherein PG is a protecting group selected from benzyloxycarbonyl (Cbz), tert-butyloxycarbonyl (Boc), phenylacetyl (PheAc), fluoren-9-ylmethoxycarbonyl (Fmoc), acetyl (Ac), benzyl (Bn), and benzoyl (Bz);
$R_5$ and $R_6$ are selected independently from —H, —OH and —($C_1$-$C_3$)alkyl;
$R_7$ is selected from —H, —OH, —CO, —NRR';
$R_8$ is selected from —H, —COO$R_9$, CONH$_2$, —CH$_2$OH, —CHO;
$R_9$ is —H, ($C_1$-$C_5$)alkyl, aryl;
wherein the alkyl and aryl moieties in $R_1$ to $R_9$ are optionally substituted with one or two groups selected independently from halogen, —OR, —NHR, —NRR';
R and R' are independently H or ($C_1$-$C_3$)alkyl.

Preferably, the compound of formula V of this particular embodiment of the invention is L-homoserine.

In a preferred embodiment of the seventh aspect of the invention, the use is further characterized by the addition of divalent metals such as $Co^{2+}$ or $Ni^{2+}$.

An eighth aspect of the invention refers to a method that comprises an aldol addition reaction of a compound of formula VII to VI catalyzed by the fusion protein or the composition as defined in the first aspect of the invention, preferably by 2-keto-3-deoxy-L-rhamnonate aldolase (YfaU, EC 4.1.2.53) from *E. coli* K12 expressed as a fusion protein with maltose binding protein (MBP), according to the following reaction scheme:

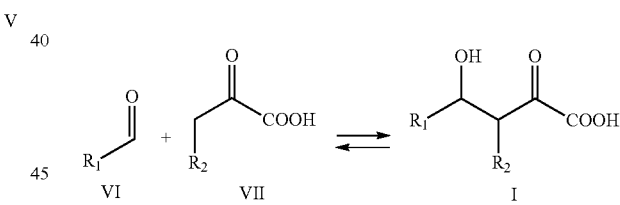

wherein $R_1$ and $R_2$ are as defined in the seventh aspect of the invention in connection to compound I.

Preferably reactants VI and VII as shown above are present in high concentrations of approx. >0.5 M, preferably >0.7 M, preferably >0.8 M, preferably >0.9 M, more preferably >1.0 M, still more preferably >1.5 M, still more preferably >1.7 M.

In a preferred embodiment of this aspect of the invention, compound VI is formaldehyde, compound VII is pyruvate or a salt thereof such as, but not limited to, sodium pyruvate and compound I is 4-hydroxy-2-oxobutanoic acid (Ia) or a salt thereof such as, but not limited to, sodium 4-hydroxy-2-oxobutanoate. Preferably these reactants are present in high concentrations of approx. >0.5 M, preferably >0.7 M, preferably >0.8 M, preferably >0.9 M, more preferably >1.0 M, still more preferably >1.5 M, still more preferably >1.7 M.

In another preferred embodiment of this aspect of the invention, the compound of formula I is any of the compounds stated in table 1 below, or any acid, salt, solvate or stereoisomer thereof.

TABLE 1

List of compounds of formula I obtained according to the methods of the present invention.

| Compound | Name |
|---|---|
| I1 | sodium 4-hydroxy-2-oxobutanoate |
| I2 | (±)-sodium 4,5-dihydroxy-2-oxopentanoate (and anomer α/β-Sodium 4-hydroxytetrahydrofuran-2-carboxylate) |
| I3a | sodium (4R,6S)-4,6-dihydroxy-2-oxoheptanoate |
| I3b | sodium (4S,6R)-4,6-dihydroxy-2-oxoheptanoate |
| I4a | sodium (5S)-5-(((benzyloxy)carbonyl)amino)-4-hydroxy-2-oxohexanoate |
| I4b | sodium (5R)-5-(((benzyloxy)carbonyl)amino)-4-hydroxy-2-oxohexanoate |
| I5 | (±)-sodium 4-hydroxy-3-(hydroxymethyl)-2-oxobutanoate |
| I6 | (±)-sodium 5-(benzyloxy)-4-hydroxy-2-oxopentanoate |
| I7a | sodium (5S)-5-(((benzyloxy)carbonyl)amino)-4-hydroxy-3-methyl-2-oxohexanoate |
| I7b | sodium (5R)-5-(((benzyloxy)carbonyl)amino)-4-hydroxy-3-methyl-2-oxohexanoate |
| I8a | sodium (5S)-5-(((benzyloxy)carbonyl)amino)-3-ethyl-4-hydroxy-2-oxohexanoate |
| I8b | sodium (5R)-5-(((benzyloxy)carbonyl)amino)-3-ethyl-4-hydroxy-2-oxohexanoate |
| I9a | sodium 3-((2S)-2-(((benzyloxy)carbonyl)amino)-1-hydroxypropyl)-2-oxooctanoate |
| I9b | sodium 3-((2R)-2-(((benzyloxy)carbonyl)amino)-1-hydroxypropyl)-2-oxooctanoate |
| I10a | sodium (5S)-5-(((benzyloxy)carbonyl)amino)-4-hydroxy-3-isopropyl-2-oxohexanoate |
| I10b | sodium (5R)-5-(((benzyloxy)carbonyl)amino)-4-hydroxy-3-isopropyl-2-oxohexanoate |
| I11 | sodium (S) 5-(((benzyloxy)carbonyl)amino)-4-hydroxy-2-oxopentanoate |
| I12a | sodium (4R,5S) 5-(((benzyloxy)carbonyl)amino)-4-hydroxy-2-oxoheptanoate |
| I12b | sodium (4S,5R) 5-(((benzyloxy)carbonyl)amino)-4-hydroxy-2-oxoheptanoate |
| I13a | sodium (4R,5S) 5-(((benzyloxy)carbonyl)amino)-4-hydroxy-6-methyl-2-oxoheptanoate |
| I13b | sodium (4S,5R) 5-(((benzyloxy)carbonyl)amino)-4-hydroxy-6-methyl-2-oxoheptanoate |
| I14a | sodium (4R,5S) 5-(((benzyloxy)carbonyl)amino)-4-hydroxy-7-methyl-2-oxooctanoate |
| I14b | sodium (4S,5R) 5-(((benzyloxy)carbonyl)amino)-4-hydroxy-7-methyl-2-oxooctanoate |
| I15a | sodium (4R,5S) 5-(((benzyloxy)carbonyl)amino)-4-hydroxy-6-methyl-2-oxooctanoate |
| I16a | sodium (S)-4-((S)-1-((benzyloxy)carbonyl)pyrrolidin-2-yl)-4-hydroxy-2-oxobutanoate |
| I16b | sodium (R)-4-((R)-1-((benzyloxy)carbonyl)pyrrolidin-2-yl)-4-hydroxy-2-oxobutanoate |
| I17a | sodium 4-((S)-1-((benzyloxy)carbonyl)pyrrolidin-2-yl)-4-hydroxy-3-methyl-2-oxobutanoate |
| I17b | sodium 4-((R)-1-((benzyloxy)carbonyl)pyrrolidin-2-yl)-4-hydroxy-3-methyl-2-oxobutanoate |
| I18a | sodium 3-((S)-1-((benzyloxy)carbonyl)pyrrolidin-2-yl)(hydroxy)methyl)-2-oxopentanoate |
| I18b | sodium 3-((R)-1-((benzyloxy)carbonyl)pyrrolidin-2-yl)(hydroxy)methyl)-2-oxopentanoate |
| I19a | sodium 3-((S)-1-((benzyloxy)carbonyl)pyrrolidin-2-yl)(hydroxy)methyl)-2-oxooctanoate |
| I19b | sodium 3-((R)-1-((benzyloxy)carbonyl)pyrrolidin-2-yl)(hydroxy)methyl)-2-oxooctanoate |

It is noted that the formation of a double-addition product (compound 1-5, i.e. sodium 4-hydroxy-3-(hydroxymethyl)-2-oxobutanoate, example 5) according to the scheme depicted above appears to be completely novel for these reactions.

In a preferred embodiment of the method according to the eighth aspect of the invention, the method further comprises the additional step of:

ii) an enzymatic reaction to obtain compounds of formula V

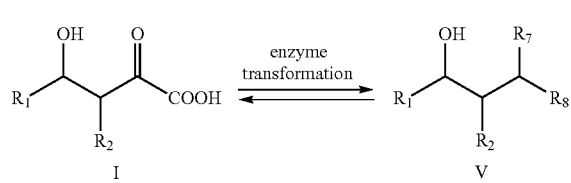

wherein $R_1$ to $R_8$ are as defined in the seventh aspect of the invention in connection to compound V.

Examples of reactions according to ii) above are, without limitation, reduction, decarboxylation or transamination using a reductase, decarboxylase or a transaminase, respectively, as shown in scheme 2.

Scheme 2. Examples of enzymatic transformations of I

In a preferred embodiment of this aspect of the invention, compound V is homoserine, preferably L-homoserine. More preferably, compound V is further reacted according to example 1 to produce L-homoserine lactone (benzyl (S)-(2-oxotetrahydrofuran-3-yl)carbamate).

Another embodiment of the present invention refers to the method according to ii) above wherein the reaction is non enzymatic, such as, but not limited to, reduction, reductive amination, lactonization, lactamization, cyclization, as shown in scheme 3 below:

Scheme 3. Examples of non-enzymatic transformations of I

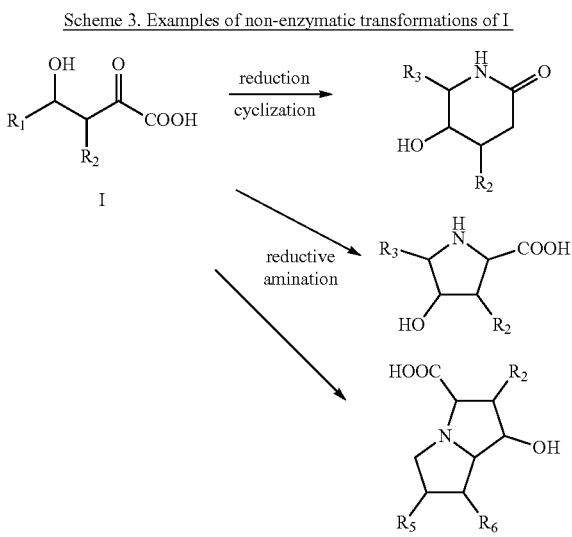

Illustrative products, falling within the scope of the present invention, resulting from the reactions according to ii) above are illustrated in table 2 below.

TABLE 2

List of compounds of formula V obtained according to the methods of the present invention.

| Compound | Name |
|---|---|
| V1 | L-homoserine |
| V4a | sodium (5S)-4-hydroxy-5-methylpyrrolidine-2-carboxylate |
| V4b | sodium (5R)-4-hydroxy-5-methylpyrrolidine-2-carboxylate |
| V12a | sodium (5S)-5-ethyl-4-hydroxypyrrolidine-2-carboxylate |
| v12b | sodium (5R)-5-ethyl-4-hydroxypyrrolidine-2-carboxylate |
| V13a | sodium (5S)-4-hydroxy-5-isopropylpyrrolidine-2-carboxylate |
| V13b | sodium (5R)-4-hydroxy-5-isopropylpyrrolidine-2-carboxylate |
| V14a | sodium (5S)-4-hydroxy-5-isobutylpyrrolidine-2-carboxylate |
| V14b | sodium (5R)-4-hydroxy-5-isobutylpyrrolidine-2-carboxylate |
| V15a | sodium (5S)-5-((S)-sec-butyl)-4-hydroxypyrrolidine-2-carboxylate |
| V16a | sodium (7aS)-1-hydroxyhexahydro-1H-pyrrolizine-3-carboxylate |
| V16b | sodium (7aR)-1-hydroxyhexahydro-1H-pyrrolizine-3-carboxylate |

In a preferred embodiment of the eighth aspect of the invention, the process is further characterized by the addition of divalent metals such as $Co^{2+}$ or $Ni^{2+}$.

A ninth aspect of the invention refers to a method for the preparation of L-homoserine, comprising the following two-step pathway:
(i) an aldol addition of preferably pyruvate to formaldehyde, catalyzed by a fusion protein enzyme or composition as described in the first aspect of the invention; and
(ii) a biocatalytic transamination reaction for the transformation of the prochiral 4-hydroxy-2-oxobutanoic acid into L-homoserine; and
optionally this method further comprises (iii) the conversion step of L-homoserine in homoserine lactone.
In a preferred embodiment of this aspect of the invention the protein fusion as illustrated in (i) above is MBP-YfaU as illustrated in SEQ ID NO 9 or in FIG. 4 and the transamination reaction is catalyzed by Prozomix TA051 or TA039 using an amine donor, preferably benzylamine.

It's worth noting that when L-Alanine is used as amine donor in the transamination step (ii), L-homoserine formation can be carried out in a one pot process of industrial interest.

A tenth aspect of the invention refers to the use of L-alanine as an amine donor in a one-pot reaction scheme using the fusion protein or composition of the first aspect of the invention.

Thus, an eleventh aspect of the invention refers to a method for the preparation of L-homoserine, comprising the following one pot pathway:
(i) adding a fusion protein enzyme or composition as described in the first aspect of the invention and a transaminase to a buffer solution;
(ii) adding L-alanine, pyruvate and PLP to the buffer solution of step (i) above;
(iii) adding formaldehyde to the composition of step (ii) above;
optionally (iv) further converting the resulting L-homoserine in (iii) in L-homoserine lactone. It is noted that step (iv) is not usually performed as part of the one pot pathway above mentioned but as an additional reaction once product (iii) (L-homoserine) is obtained.

An example of the use or process identified in aspects tenth and eleventh above is illustrated in example 1 in section B).

Furthermore, as already stated, the formation of a double-addition product (i.e. 4-hydroxy-3-(hydroxymethyl)-2-oxobutanoic acid) appears to be completely novel for these reactions. Thus, a twelfth aspect of the invention refers to a method for the preparation of double addition products, comprising an aldol addition of two compounds of formula VI to VII, preferably the double equivalents of formaldehyde to pyruvate, catalyzed by a fusion protein enzyme or composition as described in the first aspect of the invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of groups, those skilled in the art will recognize that the invention is also thereby described in terms of any individual member or subgroup of members of the group.

The project leading to this application has received funding from the European Union's Horizon 2020 research and innovation programme under grant agreement No 635595 (CarbaZymes).

EXAMPLES

Materials and methods. Cloning and expression of 2-keto-3-deoxy-L-rhamnonate aldolase (YfaU EC 4.1.2.53) of *E. coli* K-12 with maltose binding protein (MBP) to obtain MBP-YfaU.

The gene rhmA from *E coli* K-12 (NCBI database accession number NC_000913.3) was amplified by PCR from genomic DNA and cloned into pQE4OMBP (developed as discuss below) using KpnI and HindIII.

In particular, the construction of pQE40-MBP plasmid was as follows. The MBP-3C cleavage tag (Cordingley, et al. *J. Virol.* 1989, 63(12), 5037-5045) was cloned from pOPINM* plasmid as template (Berrow, N. S. et al. *Nucleic acids Res.* 2007, 35(6), e45) using the following primers: MBP-3C forward: 5'-GCTAGC<u>GGATCC</u>GGCATCATG-AAAATCGAAGAAGG-3'; MBP-3C reverse: 5"-GCTAGC<u>GCATGC</u>CGGACCCTGAAACAGAACTTCC-3'. Underlined sequences indicate the restriction sites for BamHI and SphI, respectively. The fragment was then ligated into pQE40 expression vector. The vector introduces codons for a N-terminal (His)$_6$-tag. The ligated construct was transformed into *E. coli* Nova Blue, and was confirmed by DNA sequencing.

The plasmid pQE40 MBP-YfaU was transformed into an *E. coli* strain M-15 [pREP-4] from QIAGEN and grown in LB (Luca-Bertani) medium with ampicillin (100 μg mL$^{-1}$) plus kanamycin (25 μg mL$^{-1}$) at 37° C. on a rotary shaker at 200 rpm. A final optical density at 600 nm (OD600) of 2-3 was usually achieved. An aliquot of the pre-culture (12 mL) was transferred into a shake-flask (2 L) containing LB (600 mL) with ampicillin (100 μg mL$^{-1}$) plus kanamycin (25 μg mL$^{-1}$) and incubated at 37° C. with shaking at 200 rpm. During the middle exponential phase growth (DO600≈0.5), the temperature was decreased to 20° C. to minimize potential inclusion bodies formation and isopropyl-β-D-1-thiogalactopyranoside (IPTG; 1 mM final concentration) was added. Cells from the induced-culture broths (3 L) were centrifuged at 12000 G for 30 min at 4° C. The pellet was re-suspended with starting sodium phosphate buffer (200 mL, 50 mM, pH 8.0), containing NaCl (300 mM) and imidazole (10 mM). Cells were lysed by using a cell disrupter (Constant Systems). Cellular debris was removed by centrifugation at 30 000 g for 30 min. The clear supernatant was collected and purified by immobilized metal ion affinity chromatography (IMAC) in an FPLC system (Amersham biosciences). The crude supernatant was applied to a cooled HR 16/40 column (GE Healthcare) packed with HiTrap chelating support (50 mL bed volume; Amersham Biosciences) and washed with the start buffer (250 mL). The protein was eluted with sodium phosphate buffer (50 mM, pH 8.0) containing NaCl (300 mM) and imidazole (500 mM) at a flow rate of 3 mL min$^{-1}$. Fractions containing the recombinant protein were combined and dialyzed against sodium phosphate buffer (10 mM, pH 7.0) or alternatively against sodium 3-(N-morpholino)propanesulfonate (MOPS) buffer (2 mM, pH 7.0) at 4° C. The dialyzed solution was frozen at −80° C. and lyophilized. The white solid obtained was stored at −20° C. (yield ~390 mg L$^{-1}$ of culture). FIG. 1 shows the Coomassie Blue-stained SDS-PAGE of purified MBP-YfaU.

Example 1

L-Homoserine Synthesis

A Two-step strategy using benzylamine as amine donor.

Step 1. Aldol Addition. Preparation of Sodium 4-hydroxy-2-oxobutanoate (I1)

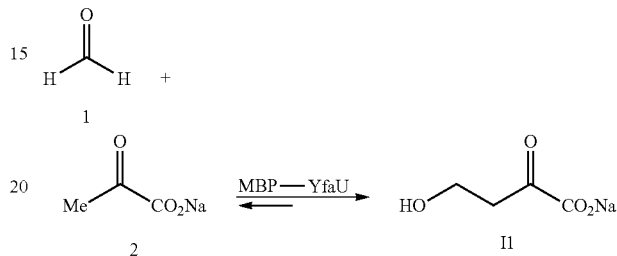

To a solution of MBP-YfaU Mg$^{2+}$ (dialyzed against sodium phosphate buffer) (15.4 mg of protein, 2 mg mL-1) containing sodium pyruvate 2 (7.1 mL, 1.0 M at pH 6.5-7.0, adjusted with NaOH, 50 mM) in a Falcon tube, formaldehyde 1 (577 μL of commercial 12.3 M solution) was added step-wise (115.4 μL each 2 h), stirring in a vortex mixer (1000 rpm) at 25° C. After 16-24 h no pyruvate was detected by HPLC (>98% conversion) and the reaction was filtered through active charcoal (in a filter funnel Pyrex 3, 5 cm Ø, filter bed 1 cm) and the pellet was washed with water (3×10 mL). Solution was frozen at −80° C. and lyophilized to afford the title compound as a white solid (442 mg as mixture of ketone I1 and its hydrate form, 44% isolated yield).

When MBP-YfaU Mg2+ was dialyzed against sodium 3-(N-morpholino)propanesulfonate (MOPS) buffer (2 mM, pH 7.0) equimolar concentration (2 M) of pyruvate and formaldehyde could be used.

Reaction monitoring was carried out as follows: samples withdrawn from the reaction mixture (10 μL, diluted to 0.1 mM of carbonyl group with MeOH) were mixed with a solution of O-benzylhydroxylamine hydrochloride (50 μL, 0.13 mM in pyridine:methanol:water 33:15:2). After incubation at 60° C. for 60 min, samples were diluted in methanol (500 μL) and after centrifugation analyzed by HPLC. Solvent system: solvent A=0.1% v/v trifluoroacetic acid (TFA) in H$_2$O; solvent B=0.095% v/v TFA in CH$_3$CN:H$_2$O 80:20. HPLC conditions: gradient elution from 10 to 100% B over 30 min; flow, 1 mL min-1; detection 215 nm.

Sodium 4-hydroxy-2-oxobutanoate (I1) $^1$H NMR (400 MHz, D$_2$O): δ (ppm) 3.71 (t, J=5.9 Hz, 2H), 2.88 (t, J=5.9 Hz, 2H). $^{13}$C NMR (101 MHz, D$_2$O): δ (ppm) 200.56 (CO), 166.37 (CO$_2$—), 55.94 (CH$_2$OH), 41.14 (CH$_2$). Sodium 2,2,4-trihydroxybutanoate (hydrate form). $^1$H NMR (400 MHz, D$_2$O): δ (ppm) 3.54 (t, J=6.7 Hz, 2H), 1.95 (t, J=6.7 Hz, 2H). $^{13}$C NMR (101 MHz, D$_2$O): δ (ppm) 174.44 (CO$^{2-}$, 118.85 (C(OH)$_2$), 56.77 (CH$_2$OH), 40.14 (CH$_2$).

Step 2. Transamination Reaction. L-homoserine (V1)

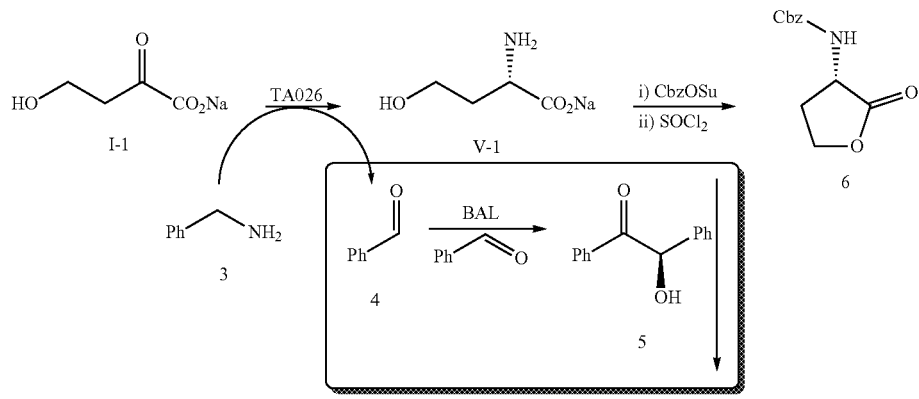

To a sodium 4-hydroxy-2-oxobutanoate (I-1) solution (8.5 mL of a 0.2 M solution in 50 mM sodium phosphate buffer pH 7.0, containing magnesium sulphate (2.5 mM), ThDP (thiamine pyrophosphate) (0.25 mM) and PLP (pyridoxal phosphate) (0.5 mM), 0.1 mol $L^{-1}$ final concentration in the reaction) in a Falcon Tube (15 mL). Benzylamine 3 (1.7 mL of a 1.0 M solution in 50 mM sodium phosphate buffer pH 7.0, 0.1 M final concentration in the reaction) was added and stirred in a vortex mixer (1000 rpm) at 25° C. The reaction was started by addition of Transaminase Prozomix TA026 (6.8 mL, 12.5 mg $mL^{-1}$ dissolved in 50 mM sodium phosphate buffer pH 7.0, containing $MgSO_4$ (2.5 mM), ThDP (0.25 mM), PLP (0.5 mM) and benzaldehyde lyase from *Pseudomonas fluorescens* biovar I (BAL) (2000 U, 5 mg $L^{-1}$ final concentration in the reaction). Reaction monitoring was carried out by HPLC. After 24 h, 71% conversion was reached. Then, the reaction was filtered through active charcoal (in a filter funnel Pyrex 3, 5 cm 0, filter bed 1 cm) and the pellet washed with $NaHCO_3$ 10% (3×20 mL). L-Homoserine (V-1) was obtained diluted in aqueous media (77 mL, 0.071 M).

Synthesis of Homoserine Lactone. Benzyl (S)-(2-oxotetrahydrofuran-3-yl)carbamate (6)

Benzyloxycarbonylsuccinimide (CbzOSu) (293 mg dissolved in $CH_3CN$ (60 mL)) was added to the filtrated containing L-homoserine (V-1) (77 mL, 0.071 M) and the reaction was stirred at 25° C. After 12 h, organic solvent was reduced under vacuum and pH of aqueous phase was adjusted to 2.0 with HCl (1 M). The aqueous solution was extracted with AcOEt (3×20 mL). The combined organic phases were dried over anhydrous $MgSO_4$ and concentrated under vacuum. The residue was dissolved in methanol (100 mL) cooled down at −80° C., and thionyl chloride (327 μL, 4.5 mmol) was added dropwise. After stirring for 12 h at 25° C., the solvent was removed under vacuum to give benzyl (S)-(2-oxotetrahydrofuran-3-yl)carbamate (6) as white solid (245 mg, 93% yield; ee>99%, $t_R$=13.3 min).

Chiral HPLC analysis: CHIRALPAK® ID 46×250 mm column, 5 μm, isocratic elution hexane/$CH_2Cl_2$/EtOH 70/10/20 (v/v/v), flow rate 0.8 mL $min^{-1}$ at 20° C., UV detection 209 and 254 nm, $t_R$ (R)=11.6 min and $t_R$ (S)=13.8 min. $[\alpha]^{20}_D$=−40.1 (c=6 in DMSO, $[\alpha]^{20}_D$ (R)=+40.8 and $[\alpha]^{20}_D$ (S)=−40.4).

$^1$H NMR (400 MHz, DMSO-$d_6$): δ (ppm) 7.77 (d, J=8.4 Hz, 1H), 7.38-7.25 (m, 5H), 4.41 (dt, J =11.3, 8.8 Hz, 1H), 4.34-4.25 (m, 1H), 4.16 (ddd, J=10.8, 8.7, 6.3 Hz, 1H), 2.43-2.32 (m, 1H), 2.14 (qd, J=11.3, 9.1 Hz, 1H). $^{13}$C NMR (101 MHz, DMSO-$d_6$): δ (ppm) 175.79 (CO), 156.17 (NHCO), 137.18 (Car), 128.81 (Car), 128.35 (Car), 128.30 (Car), 66.14 (—$CH_2$—), 65.48 (—$CH_2$—), 49.91(—CH—), 28.54 (—$CH_2^-$).

B) L-Homoserine (4). One Pot Strategy Using L-Ala as Amine Donor

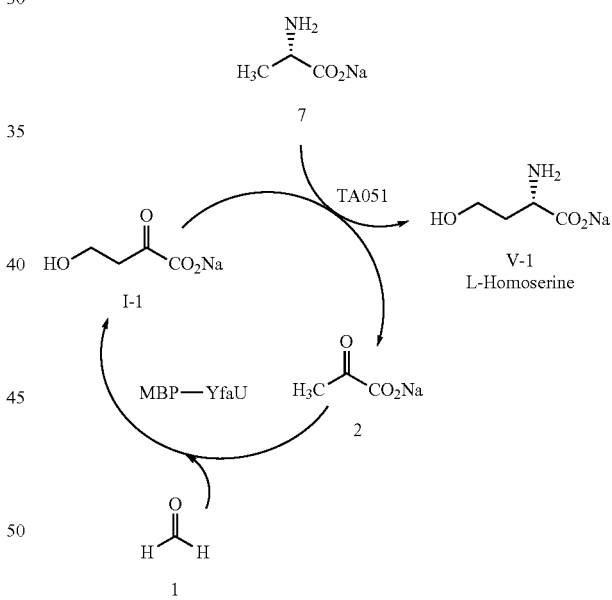

MBP-YfaU (4 mg as lyophilized powder) and transaminase Prozomix TA051 (2.8 U* as lyophilized powder) were dissolved in sodium phosphate buffer (491 μL, 50 mM, pH 7.0) in an Eppendorf tube. Then, L-Ala (267 μL of 1.5 M L-Ala solution in 50 mM sodium phosphate buffer pH 7.0, 0.4 M final concentration in the reaction), sodium pyruvate (200 μL of 1.0 M sodium pyruvate solution in 50 mM sodium phosphate buffer pH 7.0, 0.2 M final concentration in the reaction) and PLP (10 μL of 100 mM PLP solution in 50 mM sodium phosphate buffer pH 7.0, 1 mM final concentration in reaction) were added. The reaction mixture was placed in a vortex mixer (1000 rpm) at 25° C. The reaction was initiated by slow addition of formaldehyde (4 μL of 12.3 M solution every 1 h, 8 additions, 32 μL total volume added). Reaction monitoring was carried out by HPLC and the product was quantified using an external standard method. After 24 h the yield of L-homoserine was 50% respect to the amount of formaldehyde.

Example 2

(±)-Sodium 4-hydroxytetrahydrofuran-2-carboxylate (α/β-I-2)

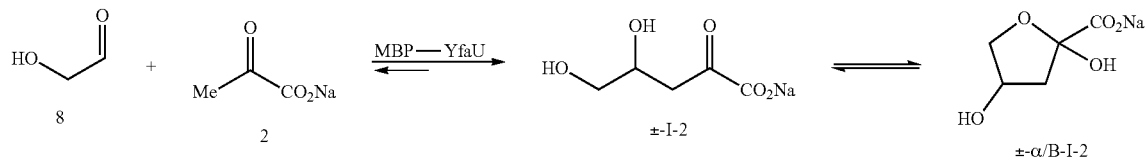

Reaction was carried out in a Falcon Tube (15 mL). Sodium pyruvate (2) (0.65 g, 5.9 mmol) was dissolved in water (6 mL). Glycolaldehyde (8) (0.35 mg of the commercially available dimer corresponding to 5.9 mmol of monomer) was added to this solution and the pH was adjusted to 7.0 with NaOH (50 mM). The reaction was initiated by the addition of MBP-YfaU as lyophilized powder (30 mg). The mixture was left to react under orbital stirring (1000 rpm) at 25° C. for 16 h. The reaction conversion at this point was greater than 95%, as judged by HPLC analysis. Then, the reaction was centrifuged (5000 g at 4° C. for 30 minutes) and the enzyme in the supernatant, was removed using an Amicon ultrafiltration unit (Millipore, USA, MWCO 10 kDa, 5000 g at 4° C. for 60 minutes) and the residue washed with water (3×6 mL). The combined aqueous phase was frozen at −80° C. and lyophilized to afford the title compound as a white solid (0.98 g, 98% corresponding to a mixture of the (α/β)-anomer (±-(α/⊕)-I-2) and the acyclic compound ((±)-I-2) in 1:1 proportion).

NMR (α-Anomer). $^1$H NMR (400 MHz, $D_2O$): δ (ppm) 4.58 (m, 1H), 4.16 (dd, J=9.6, 4.1 Hz, 1H), 3.92 (dd, J=9.6, 2.2 Hz, 1H), 2.3 (t, J=4.6 Hz, 1H). 13C NMR (101 MHz, $D_2O$): δ (ppm) 176.9, 103.8, 74.9, 71.3, 44.1. (β-Anomer). $^1$H NMR (400 MHz, $D_2O$): δ(ppm) 4.58 (m, 1H), 4.13 (m, 1H), 4.03 (dd, J=9.8, 2.5 Hz, 1H), 2.48 (dd, J=14.3, 6.2 Hz, 1H), 2.08 (dd, J=14.2, 2.2 Hz, 1H). $^{13}$C NMR (101 MHz, $D_2O$): δ (ppm) 176.8, 103.8, 75.5, 70.5, 43.8. (Acyclic I-2) $^1$H NMR (400 MHz, $D_2O$): δ (ppm) 4.22 (ddt, J=8.4, 6.5, 4.4 Hz, 1H), 3.63 (dd, J=11.8, 4.2 Hz, 1H), 3.56 (dd, J=11.8, 6.4 Hz, 1H), 2.99 (dd, J=17.1, 4.5 Hz, 1H), 2.92 (dd, J=17.1, 8.2 Hz, 1H). $^{13}$C NMR (101 MHz, $D_2O$): δ (ppm) 203.6, 169.5, 67.4, 64.9, 42.8.

Example 3

Sodium (4R,6S)-2,4-dihydroxy-6-methyltetrahydro-2H-pyran-2-carboxylate (13)

Step 1. Synthesis (S)-3-hydroxybutanal (9)

(S)-3-Hydroxybutanal (9) was obtained from (S)-4,4-dimethoxybutan-2-ol by acid hydrolysis as described below. (S)-4,4-Dimethoxybutan-2-ol was obtained from stereoselective reduction of 4,4-dimethoxybutan-2-one.

(S)-4,4-Dimethoxybutan-2-ol (1.28 g, 9.5 mmol) was dissolved in water (10 mL) and Dowex® 50WX8 hydrogen form, 200-400 mesh, (2 g as dry powder) was added. The mixture was left to react under orbital stirring (1000 rpm). After 12 h, when most of the reactant was consumed as judged by TLC, the reaction was filtered and resin was washed with water (5 mL). The aldehyde 12 obtained was used in solution (0.5 M, 17 mL) without any further purification.

Step 2. Preparation of adduct I-3a

To a solution of (S)-3-hydroxybutanal (9) (11.2 mL, 5.6 mmol) sodium pyruvate (5.6 mL of 1.0 M sodium pyruvate solution in 50 mM sodium phosphate buffer pH 7.0) was added in a falcon tube. The reaction was initiated by addition of $NiCl_2$ (0.17 mL of 0.1 M $NiCl_2$ solution in water) and MBP-YfaU as lyophilized powder (96 mg). The mixture (16.8 mL) was left to react under orbital stirring (1000 rpm) at 25° C. for 16 h. The reaction conversion at this point was greater than 95%, as judged by HPLC. Then, the reaction mixture was diluted with methanol (168 mL), filtered through Celite® and the pellet washed with methanol (3×50 mL). The filtrate was then adsorbed onto silica gel (40 g), dried under vacuum and loaded on a silica column chromatography (I=47 cm and (I)=4.5 cm with 200 mL of silica gel). The product was eluted with a step gradient of $CHCl_3$:MeOH:$H_2O$, 100:0:0, 200 mL, 75:25:0, 200 mL, 50:50:0, 400 mL, 48:48:4, 400 mL and 45:45:10, 1000 mL. Pure fractions were pooled and the solvent removed under vacuum affording the sodium (4R,6S)-4,6-dihydroxy-2-oxoheptanoate (I-3a) as a yellow oil (0.95 g, 95%).

$[α]^{20}_D$=−18.6 (c=5.0 in DMSO). (α-Anomer): $^1$H NMR (400 MHz, $D_2O$): δ (ppm) 4.06-4.08 (m, 2H), 2.10 (ddd, J=12.6, 4.7, 2.0 Hz, 1H), 2.04 (ddt, J=12.4, 4.3, 2.1 Hz, 1H), 1.62 (dd, J =12.6, 11.5 Hz, 1H), 1.27 (m, 1H), 1.24 (d, J=3.8 Hz, 1H). $^{13}$C NMR (101 MHz, $D_2O$): δ (ppm) 176.2, 96.6, 66.6, 63.9, 40.7, 39.5, 20.4. (β-Anomer): $^1$H NMR (400 MHz, $D_2O$): δ (ppm) 3.97 (m, 1H), 3.71 (m, 1H), 2.52 (dd, J=7.1, 1.3 Hz, 1H), 1.98 (dt, J=4.4, 1.9 Hz, 1H), 1.22 (m, 1H), 1.16 (m, 3H), 1.09 (m, 1H). $^{13}$C NMR (101 MHz, $D_2O$): δ (ppm) 176.4, 97.1, 68.4, 65.1, 41.0, 40.3, 20.6.

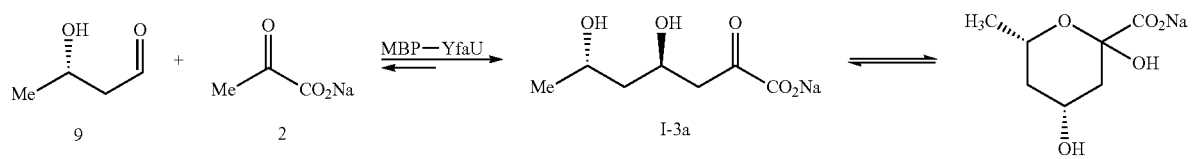

Example 4

Sodium 4-hydroxy-5-methylpyrrolidine-2-carboxylate (V-4)

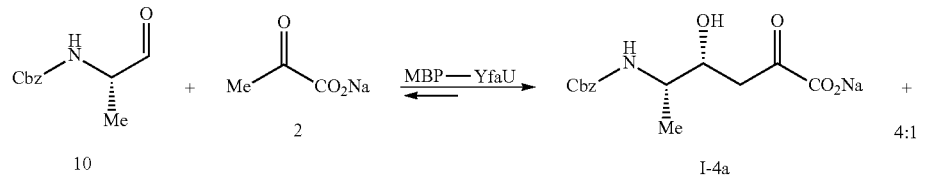

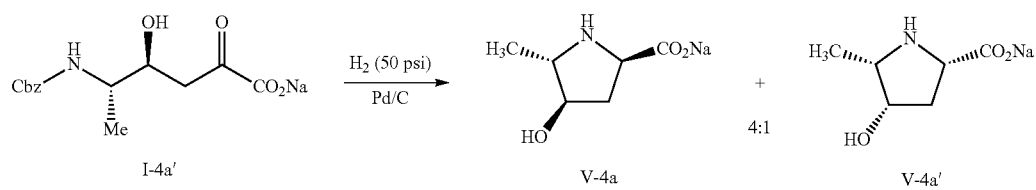

Starting aldehyde, benzyl (S)-(1-oxopropan-2-yl)carbamate (10), was obtained from (S)-2-aminopropanal by conventional processes.

Step 1. Preparation of (4R,5S)-(I-4a) and (4S,5S)-5-(((benzyloxy)carbonyl)amino)-4-hydroxy-2-oxohexanoate (I-4a')

To a solution of (S)—N-Cbz-alaninal (10) (0.5 g, 2.5 mmol) in dimethylformamide (DMF) (5 mL), sodium borate buffer (8.8 mL, 50 mM, pH 7.0) was added. Then, sodium pyruvate (2.5 mL of 1.0 M sodium pyruvate solution in 50 mM sodium borate buffer pH 7.0) and $NiCl_2$ (0.25 mL of 0.1 M $NiCl_2$ solution in water) were added. The reaction was initiated by the addition of MBP-YfaU as lyophilized powder (63 mg) dissolved in sodium borate buffer (8.8 mL, 50 mM, pH 7.0). The mixture (25 mL) was left to react under orbital stirring (1000 rpm) for 16 h. The reaction conversion at this point was greater than 95%, as judged by HPLC. Then, the reaction mixture was diluted with methanol (250 mL), filtered through Celite® and the pellet washed with methanol (3×50 mL). The filtrate was adsorbed onto silica gel (40 g) and loaded onto a silica column chromatography (I=47 and φ=4.5 cm with 200 mL of silica gel). The product was eluted with a step gradient of $CHCl_3$:MeOH, 100:0, 200 mL, 90:10, 200 mL, 75:25, 400 mL and 50:50, 600 mL. Pure fractions were pooled and the solvent removed under vacuum affording the sodium (4R,5S)-(I-4a) and (4S,5S)-5-(((benzyloxy)carbonyl)amino)-4-hydroxy-2-oxohexanoate (I-4a'). 4:1 mixture as white solid (0.68 g, 85%). $[\alpha]^{20}_D = -6.2$ (c=5.0 in DMSO).

To unequivocally acess the structure and stereochemistry of the aldol adduct and produce an amino acid of the pyrrolidine type derivative, the aldol product mixture was submitted to reductive amination.

Step 2. Preparation of Sodium 4-hydroxy-5-methylpyrrolidine-2-carboxylate (V-4a-a')

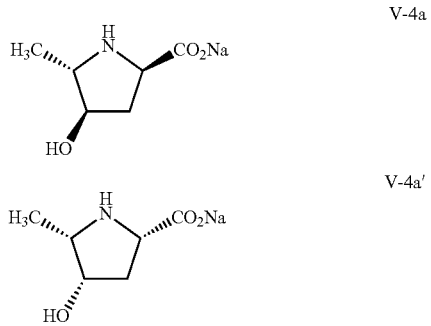

The adduct I-4 (0.3 g, 0.9 mmol) was dissolved in MeOH/$H_2O$ 6:1 (700 mL). The solution was kept under $H_2$ atmosphere at 50 psi in the presence of palladium over charcoal (Pd/C) (1 g).

After 12 h the reaction was filtered through Celite® and the pellet was washed with water (3×50 mL). The solution was concentrated under vacuum, frozen at −80° C. and lyophilized to afford compounds V-4 a and a' (150 mg as mixture of diastereomers, (2R,4R,5S): (2S,4S,5S) V-4a:V-4a' 4:1). $[\alpha]^{20}_D = +7.5$ (c=1.0 in water).

(V-4a Major) $^1H$ NMR (500 MHz, $D_2O$): δ (ppm) 4.23 (dd, J=10.0, 6.0 Hz, 1H), 4.19 (q, J=4.7 Hz, 1H), 3.73 (qd, J=7.0, 4.1 Hz, 1H), 2.70 (ddd, J=14.0, 9.8, 5.4 Hz, 1H), 2.11 (dt, J=14.0, 5.2 Hz, 1H), 1.34 (d, J=7.0 Hz, 4H). $^{13}C$ NMR (101 MHz, $D_2O$): δ (ppm) 166.6, 74.3, 61.3, 57.9, 35.3, 14.3. (V-4a' Minor): $^1H$ NMR (500 MHz, $D_2O$): δ (ppm) 4.32 (m, 1H), 4.19 (m, Hz, 1H), 3.68 (m, 1H), 2.58 (ddd, J=15.0, 11.0, 4.5 Hz, 1H), 2.26 (m, 1H), 1.41 (d, J=6.8 Hz, 2H). $^{13}C$ NMR (101 MHz, $D_2O$): δ (ppm) 166.6, 70.5, 60.8, 59.0, 37.0, 11.1.

Example 5

Preparation of Sodium
4-hydroxy-3-(hydroxymethyl)-2-oxobutanoate (I-5)

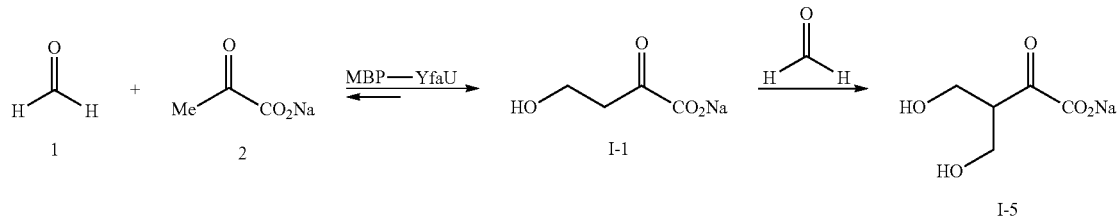

Formaldehyde (691 μL of 12.3 M commercial solution) was dissolved in 50 mM sodium phosphate buffer pH 7.0 (2.15 mL, containing 2.0 M of sodium pyruvate) in a Falcon tube. The reaction was started by the addition of MBP-YfaU (2.15 mL, 2 mg mL$^{-1}$ final concentration in reaction, dissolved in 50 mM sodium phosphate buffer pH 7.0, containing 2.0, M of sodium pyruvate) and NiCl$_2$ (1 mM final concentration in reaction). The reaction was placed in vortex mixer (1000 rpm) at 25° C. Reaction monitoring was carried out by HPLC as described in example 1. After 12 h MeOH (50 mL) was added to the reaction and mixture was filtered through Celite and the pellet was washed with MeOH (3×50 mL). The product was absorbed onto silica (100 mL) and purified by flash chromatography using silica gel (CH$_2$Cl$_2$/MeOH:H$_2$O, 5:5:1) to afford the title compound 1-5 as a white solid (485 mg, 50% as sodium salt).

I-5: $^1$H NMR (400 MHz, D$_2$O): δ (ppm) 3.83-3.66 (m, 4H), 3.26 (t, J=5.7 Hz, 1H). $^{13}$C NMR (101 MHz, D$_2$O): δ (ppm) 205.35, 58.53, 52.69.

Example 6

Preparation of Xompounds I6-I19

General procedure: To a solution of the appropriate N-Cbz-aminoaldehyde 10 or 12 (Table 3) (2.5 mmol) in DMF (5 mL), sodium borate buffer (8.8 mL, 50 mM, pH 7.0) was added. Then, pyruvate or pyruvate analogs 2 (2.5 mmol in 50 mM sodium borate buffer pH 7.0) and NiCl$_2$ (0.25 mL of 0.1 M NiCl$_2$ solution in water) were added. The reaction was initiated by the addition of MBP-YfaU or the corresponding variant as lyophilized powder (63 mg) dissolved in sodium borate buffer (8.8 mL, 50 mM, pH 7.0). The mixture (25 mL) was left to react under orbital stirring (1000 rpm) for 24 h. Then, the reaction mixture was diluted with methanol (250 mL), filtered through Celite® and the pellet washed with methanol (3×50 mL). The filtrate was adsorbed onto silica gel (40 g) and loaded onto a silica column chromatography (l=47 and ϕ=4.5 cm with 200 mL of silica gel). The products were eluted with a step gradient of CHCl$_3$:MeOH, 100:0, 200 mL, 90:10, 200 mL, 75:25, 400 mL and 50:50, 600 mL. Pure fractions were pooled and the solvent removed under vacuum.

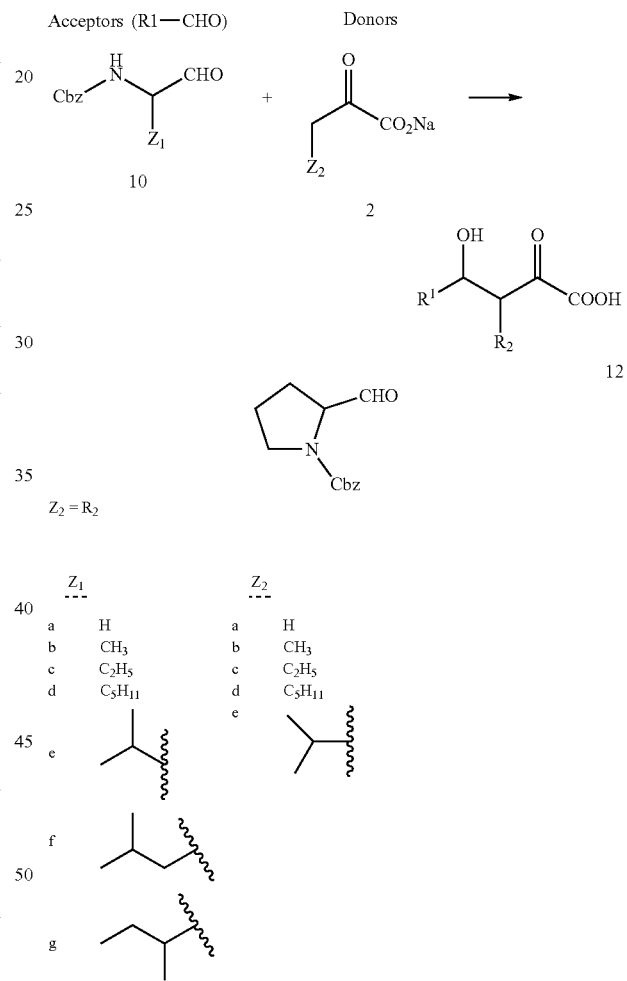

TABLE 3

Preparation of compounds I6-I19

| Compound | Acceptor | Donor | Conv/% | Yield** |
|---|---|---|---|---|
| I1 | 1 | 2a | >95 | |
| I2 | 8 | 2a | >95 | 99 |
| I3a | 9-(S) | 2a | >95 | 98 |
| I3b | 9-(R) | 2a | 73 | 72 |
| I4a | 10b-(S) | 2a | >95 | 85 |
| I4b | 10b-(R) | 2a | >95 | 77 |

TABLE 3-continued

Preparation of compounds I6-I19

| Compound | Acceptor | Donor | Conv/% | Yield** |
|---|---|---|---|---|
| I5 | 1 | I1 | 50 | |
| I6 | 8Bn | 2a | 81 | 53 |
| I7a | 10b-(S) | 2b | 70 | |
| I7b | 10b-(R) | 2b | 79 | |
| I8a | 10b-(S) | 2c | 20-30 | |
| I8b | 10b-(R) | 2c | 35 | |
| I9a | 10b-(S) | 2d | 31* | |
| I9b | 10b-(R) | 2d | 51* | |
| I10a | 10b-(S) | 2e | 53* | |
| I10b | 10b-(R) | 2e | 63* | |
| I11 | 10a | 2a | >95 | 47 |
| I12a | 10c-(S) | 2a | >95 | 81 |
| I12b | 10c-(R) | 2a | >95 | 71 |
| I13a | 10e-(S) | 2a | >95 | 86 |
| I13b | 10e-(R) | 2a | >95 | 91 |
| I14a | 10f-(S) | 2a | 53 | 50 |
| I14b | 10f-(R) | 2a | 51 | 47 |
| I15a | 10g-(S) | 2a | 63 | 60 |
| I16a | 12-(S) | 2a | 91 | 69 |
| I16b | 12-(R) | 2a | 88 | 70 |
| I17a | 12-(S) | 2b | 77 | |
| I17b | 12-(R) | 2b | 54 | |
| I18a | 12-(S) | 2c | 19 | |
| I18b | 12-(R) | 2c | 32 | |
| I19b | 12-(R) | 2d | 20* | |

*Not native MPB-YfaU was used
**Isolated yield. When yield is not mentioned no isolation was achieved

Example 7

Preparation of Compounds V4 and V12-V16

Reductive amination of compounds I4 and I-12-I-16 to obtain compounds V4 and V12-V-16 following similar conditions as in example 4 step 2. General procedure: The adducts I (0.9 mmol) were dissolved in MeOH/H$_2$O 6:1 (700 mL). The solution was kept under H$_2$ atmosphere at 50 psi in the presence of palladium over charcoal (Pd/C) (1 g). After 12 h the reaction was filtered through Celite® and the pellet was washed with water (3×50 mL). The solution was concentrated under vacuum, frozen at −80° C. and lyophilized to afford compounds V (Table 4).

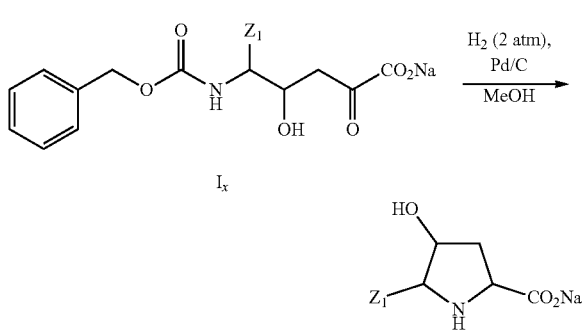

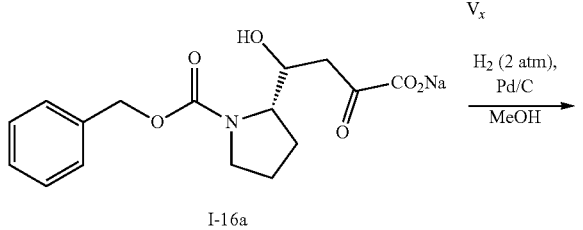

I-16a

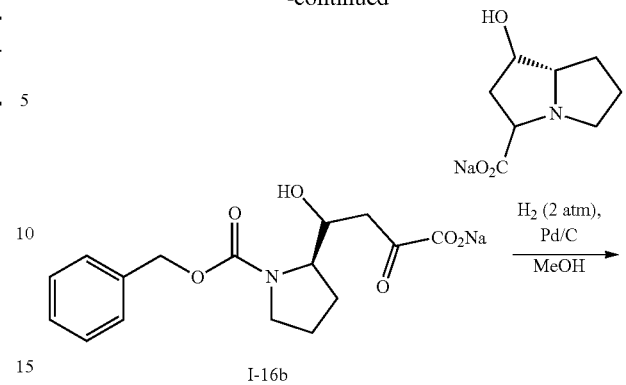

I-16b

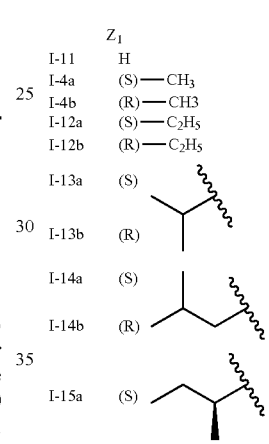

| | Z$_1$ |
|---|---|
| I-11 | H |
| I-4a | (S)—CH$_3$ |
| I-4b | (R)—CH3 |
| I-12a | (S)—C$_2$H$_5$ |
| I-12b | (R)—C$_2$H$_5$ |
| I-13a | (S) |
| I-13b | (R) |
| I-14a | (S) |
| I-14b | (R) |
| I-15a | (S) |

TABLE 4

Compounds V$_x$ obtained from I$_x$

| Compound | Yield (%) | [α]$_λ$ |
|---|---|---|
| V-4a | >90 | +7.5 |
| V-4b | >90 | −6.3 |
| V-12a | >90 | +6.8 |
| V-12b | >90 | −3.5 |
| V-13a | >90 | +10.4 |
| V-13b | >90 | −6.0 |
| V-14a | >90 | +6.0 |
| V-14b | >90 | −2.6 |
| V-15a | >90 | |
| V-16a | >90 | +14.4 |
| V-16b | >90 | −13.2 |

Example 8

MBP-YfaU Variants

Following the reaction schemes depicted below, and using the appropriate reactant compounds shown below we prepared compounds of formula I by using the native MBP-YfaU protein and its variants thereof as referred to in the first aspect of the invention:

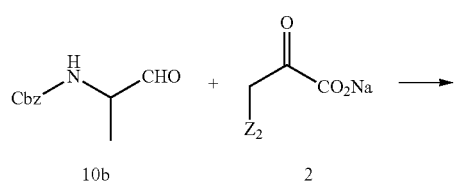

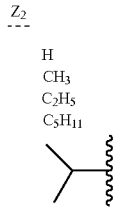

| Z$_2$ | |
|---|---|
| a | H |
| b | CH$_3$ |
| c | C$_2$H$_5$ |
| d | C$_5$H$_{11}$ |
| e | (isopropyl/isobutyl group) |

The results are illustrated in table V below.

TABLE 5

Reactions with 10b carried out using MBP-YfaU being YfaU in its native form or its variants

| | | YfaU native | | YfaU W23V | |
|---|---|---|---|---|---|
| Comp | (2) | 10b-(R) Conv (%) | 10b-(S) Conv (%) | 10b-(R) Conv (%) | 10b-(S) Conv (%) |
| I-4(b,a) | a | >95 | >95 | >95 | >95 |
| I-7(b,a) | b | 79 | 70 | 88 | 80 |
| I-8(b,a) | c | 35 | 20-30 | >95 | >95 |
| I-9(b,a) | d | — | — | 5 | — |
| I-10(b,a) | e | — | — | 24 | 5 |

TABLE 5-continued

Reactions with 10b carried out using MBP-YfaU being YfaU in its native form or its variants

| | | YfaU L216A | | YfaU W23V L216A | |
|---|---|---|---|---|---|
| Comp | (2) | 10b-(R) Conv (%) | 10b-(S) Conv (%) | 10b-(R) Conv (%) | 10b-(S) Conv (%) |
| I-4(b,a) | a | >95 | >95 | >95 | >95 |
| I-7(b,a) | b | 11 | 19 | 93 | 76 |
| I-8(b,a) | c | 27 | 18 | >95 | >95 |
| I-9(b,a) | d | — | — | 29 | 11 |
| I-10(b,a) | e | — | — | 63 | 56 |

| | | YfaU W23VF174VL216A | | YfaU W23AL216A | |
|---|---|---|---|---|---|
| Comp | (2) | 10b-(R) Conv (%) | 10b-(S) Conv (%) | 10b-(R) Conv (%) | 10b-(S) Conv (%) |
| I-4(b,a) | a | >95 | >95 | >95 | >95 |
| I-7(b,a) | b | 32 | 33 | 42 | 34 |
| I-8(b,a) | c | 27 | 18 | >95 | >95 |
| I-9(b,a) | d | 28 | 28 | 51 | 31 |
| I-10(b,a) | e | — | — | 28 | 38 |

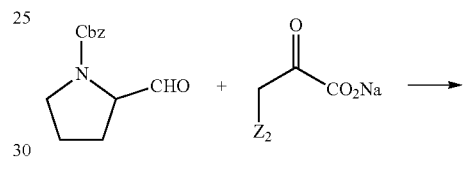

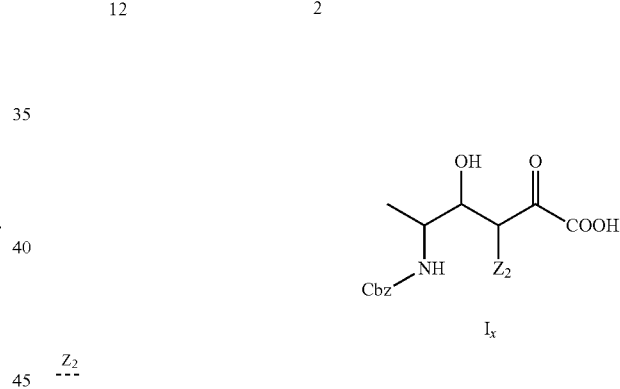

| Z$_2$ | |
|---|---|
| b | CH$_3$ |
| c | C$_2$H$_5$ |
| d | C$_5$H$_{11}$ |

The results are illustrated in table 6 below.

TABLE 6

Reactions with 12 carried out using MBP-YfaU being YfaU in its native form or its variants

| | | YfaU native | | YfaU W23V | | YfaU L216A | | YfaU W23V L216A | |
|---|---|---|---|---|---|---|---|---|---|
| Comp | (2) | 12-(R) Conv (%) | 12-(S) Conv (%) | 12-(R) Conv (%) | 12-(S) Conv (%) | 12-(R) Conv (%) | 12-(S) Conv (%) | 12-(R) Conv (%) | 12-(S) Conv (%) |
| I-17(b,a) | b | 54 | 77 | 55 | 62 | 34 | 66 | 51 | 80 |
| I-18(b,a) | c | 32 | 19 | 44 | 22 | 29 | 21 | 39 | 39 |
| I-19(b,a) | d | — | — | 7 | — | — | — | 20 | 6 |

The invention claimed is:

1. A composition comprising a fusion protein which in turn comprises a 2-keto-3-deoxy-L-rhamnonate aldolase or a variant thereof, wherein the term "variant—is understood as a protein exhibiting 2-keto-3-deoxy-L-rhamnonate aldolase activity and at least 90% sequence identity with amino acid sequence SEQ ID NO 1 or with an amino acid sequence coded by SEQ ID NO 2 bound to, optionally through a peptide linker, a maltose binding protein (MBP)
wherein the fusion protein retains full activity under denaturing conditions comprising high formaldehyde and pyruvate concentration of 1M to up to 1.7 M.

2. The composition of claim 1, wherein said aldolase is bound to the MBP through a peptide linker having from 3 to 50 amino acids in length.

3. The composition of claim 1, wherein the MBP is the MBP of SEQ ID NO 8, or a variant thereof, wherein the variant is a protein exhibiting at least 80% sequence identity with the MBP having amino acid sequence SEQ ID NO 8.

4. The composition of claim 3, wherein the aldolase is the 2-keto-3-deoxy-L-rhamnonate aldolase consisting of SEQ ID NO 1, and the MBP is the MBP of SEQ ID NO 8.

5. The composition of claim 1, wherein said composition further comprises any of the following components: protein divalent metals, additional enzymes or any combination thereof.

6. A fusion or polynucleotide sequence coding for the fusion protein of claim 1.

7. A plasmid or vector comprising the fusion or polynucleotide sequence of claim 6.

8. A prokaryotic or eukaryotic microorganism modified, transformed, transduced or transfected with the plasmid or vector of claim 7.

9. A method for the synthesis of hydroxyketoacids of formula I comprising an aldol reaction of at least a compound of formula VI to VII catalyzed by the composition of claim 1, according to the following reaction scheme:

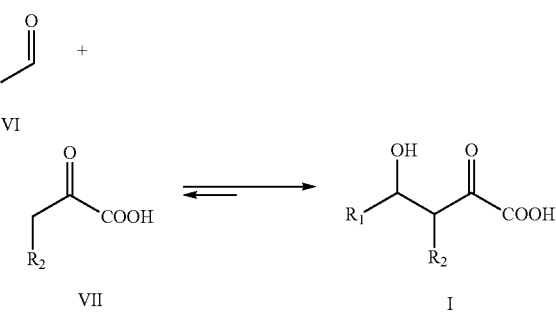

or any stereoisomers, salts or solvates thereof;
wherein
$R_1$ is selected from —H, —$(C_1$-$C_6)$alkyl, —$(C_0$-$C_3)$alkylaryl, —$(CH_2)_m OCH_2$aryl, wherein m is an integer number from 1 to 6, and substituents of formula II, III or IV:

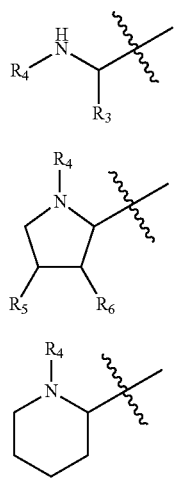

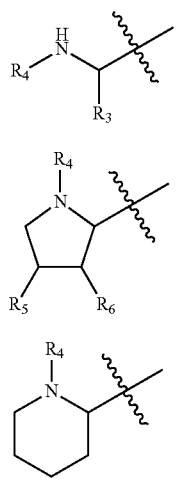

R₂ is selected from —H, —OH, and —(C₁-C₆)alkyl;
R₃ is selected from —H, —(C₁-C₈)alkyl, and —(C₀-C₃)alkylaryl;
R₄ is selected from —H and -PG, wherein PG is a protecting group selected from benzyloxycarbonyl (Cbz), tert-butyloxycarbonyl (Boc), phenylacetyl (PheAc), fluoren-9-ylmethoxycarbonyl (Fmoc), acetyl (Ac), benzyl (Bn), and benzoyl (Bz);
R₅ and R₆ are selected independently from —H, —OH and —(C₁-C₃)alkyl; and
wherein the alkyl and aryl moieties in R₁, R₂ and R₃ are optionally substituted—with one or two groups selected independently from halogen, —OR, —NHR, —NRR' being R and R' selected from —H and a —(C₁-C₃)alkyl.

10. The method of claim 9, wherein compound VI is formaldehyde, compound VII is pyruvate, or a salt thereof, and compound I is 4-hydroxy-2-oxobutanoic acid, or a salt thereof.

11. The method of claim 10, wherein each of the reactants are present in a concentration greater than 1 M.

12. The method of claim 9, which further comprises the additional step of:
(i) an enzymatic reaction to obtain compounds of formula V

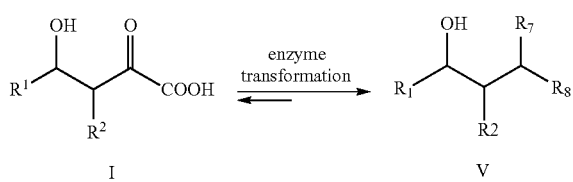

wherein
R₁ is selected from —H, —(C₁-C₆)alkyl, —(C₀-C₃)alkylaryl, (CH₂)ₘOCH₂aryl, wherein m is an integer number from 1 to 6, and substituents of formula II, III or IV:

R₂ is selected from —H, —OH, and- —(C₁-C₆)alkyl;
R₃ is selected from —H, - —(C₁-C₈)alkyl, and a —(C₀-C₃)alkylaryl;
R₄ is selected from —H and -PG, wherein PG is a protecting group selected from benzyloxycarbonyl (Cbz), tert-butyloxycarbonyl (Boc), phenylacetyl (PheAc), fluoren-9-ylmethoxycarbonyl (Fmoc), acetyl (Ac), benzyl (Bn), and benzoyl (Bz);
R₅ and R₆ are selected independently from —H, —OH and —(C₁-C₃)alkyl;
R₇ is selected from —H, —OH, —CO, —NRR';
R₉ is selected from —H, —COOR₉, CONH₂, —CH₂OH, —CHO;
R₉ is —H, (C₁-C₅)alkyl, aryl;
wherein the alkyl and aryl moieties in R₁ to R₉ are optionally substituted with one or two groups selected independently from halogen, —OR, —NHR and —NRR';
R and R' are independently H or (C₁-C₃)alkyl.

13. The method of claim 9, which further comprises the additional step of:
a non-enzymatic reaction to obtain compounds of formula V from compound of formula I wherein the non-enzymatic reaction comprises a reduction, reductive amination, lactonization, lactamization, or cyclization reaction.

14. The method of claim 12, wherein compound V is homoserine.

15. The composition of claim 5, wherein said protein divalent metals, are selected from Mg²⁺, Co²⁺ and Ni²⁺.

16. The composition of claim 5, wherein said additional enzymes are selected from reductases, decarboxylases and transaminases.

17. The composition of claim 16, wherein said transaminase comprises the transaminase Prozomix TA051.

18. The composition of claim 17, wherein said transaminase Prozomix TA051 is in the form of a lyophilized cell free extract powder.

19. The method of claim 14, wherein the homoserine is L-homoserine.

* * * * *

UNITED STATES PATENT AND TRADEMARK OFFICE
CERTIFICATE OF CORRECTION

PATENT NO. : 10,683,493 B2
APPLICATION NO. : 16/302439
DATED : June 16, 2020
INVENTOR(S) : Pedro Clapés Saborit et al.

Page 1 of 1

It is certified that error appears in the above-identified patent and that said Letters Patent is hereby corrected as shown below:

In the Claims

Column 72, Line 33:
"$R_9$ is selected from –H, –COOR$_9$, CONH$_2$, –CH$_2$OH," should read, --$R_8$ is selected from –H, –COOR$_9$, CONH$_2$, –CH$_2$OH,--.

Signed and Sealed this
Third Day of November, 2020

Andrei Iancu
*Director of the United States Patent and Trademark Office*

SEQUENCE LISTING

<160> NUMBER OF SEQ ID NOS: 17

<210> SEQ ID NO 1
<211> LENGTH: 267
<212> TYPE: PRT
<213> ORGANISM: Escherichia coli
<220> FEATURE:
<223> OTHER INFORMATION: EC 4.1.2.53, 2-keto-3-deoxy-L-rhamnonate
      aldolase

<400> SEQUENCE: 1

Met Asn Ala Leu Leu Ser Asn Pro Phe Lys Glu Arg Leu Arg Lys Gly
1               5                   10                  15

Glu Val Gln Ile Gly Leu Trp Leu Ser Ser Thr Thr Ala Tyr Met Ala
            20                  25                  30

Glu Ile Ala Ala Thr Ser Gly Tyr Asp Trp Leu Leu Ile Asp Gly Glu
        35                  40                  45

His Ala Pro Asn Thr Ile Gln Asp Leu Tyr His Gln Leu Gln Ala Val
    50                  55                  60

Ala Pro Tyr Ala Ser Gln Pro Val Ile Arg Pro Val Glu Gly Ser Lys
65                  70                  75                  80

Pro Leu Ile Lys Gln Val Leu Asp Ile Gly Ala Gln Thr Leu Leu Ile
                85                  90                  95

Pro Met Val Asp Thr Ala Glu Gln Ala Arg Gln Val Val Ser Ala Thr
            100                 105                 110

Arg Tyr Pro Pro Tyr Gly Glu Arg Gly Val Gly Ala Ser Val Ala Arg
        115                 120                 125

Ala Ala Arg Trp Gly Arg Ile Glu Asn Tyr Met Ala Gln Val Asn Asp
    130                 135                 140

Ser Leu Cys Leu Leu Val Gln Val Glu Ser Lys Thr Ala Leu Asp Asn
145                 150                 155                 160

Leu Asp Glu Ile Leu Asp Val Glu Gly Ile Asp Gly Val Phe Ile Gly
                165                 170                 175

Pro Ala Asp Leu Ser Ala Ser Leu Gly Tyr Pro Asp Asn Ala Gly His
            180                 185                 190

Pro Glu Val Gln Arg Ile Ile Glu Thr Ser Ile Arg Arg Ile Arg Ala
        195                 200                 205

Ala Gly Lys Ala Ala Gly Phe Leu Ala Val Ala Pro Asp Met Ala Gln
    210                 215                 220

Gln Cys Leu Ala Trp Gly Ala Asn Phe Val Ala Val Gly Val Asp Thr
225                 230                 235                 240

Met Leu Tyr Ser Asp Ala Leu Asp Gln Arg Leu Ala Met Phe Lys Ser
                245                 250                 255

Gly Lys Asn Gly Pro Arg Ile Lys Gly Ser Tyr
            260                 265

<210> SEQ ID NO 2
<211> LENGTH: 804
<212> TYPE: DNA
<213> ORGANISM: Escherichia coli
<220> FEATURE:
<223> OTHER INFORMATION: Gene sequence of EC 4.1.2.53, 2-keto-3-deoxy-L-
      rhamnonate aldolase

<400> SEQUENCE: 2
atgaacgcat tattaagcaa tccctttaaa gaacgtttac gcaagggcga agtgcaaatt      60
ggtctgtggt taagctcaac gactgccnat atggcagaaa ttgccgccac ttctggttat    120

```
gactggttgc tgattgacgg ggagcacgcg ccaaacacca ttcaggatct ttatcatcag    180
ctacaggcgg tagcgcccta tgccagccaa cccgtgatcc gtccggtgga aggcagtaaa    240
ccgctgatta aacaagtcct ggatattggc gcgcaaactc tactgatccc gatggtcgat    300
actgccgaac aggcacgtca ggtggtgtct gccacgcgct atcctcccta cggtgagcgt    360
ggtgtcgggg ccagtgtggc acgggctgcg cgctgggac gcattgagaa ttacatggcg     420
caagttaacg attcgctttg tctgttggtg caggtggaaa gtaaaacggc actggataac    480
ctggacgaaa tcctcgacgt cgaagggatt gatggcgtgt tattggacc tgcggatctt     540 tctgcgtcgt tgggctaccc ggataacgcc gggcacccgg aagtgcagcg aattattgaa    600
accagtattc ggcggatccg tgctgcgggt aaagcggctg gttttctggc tgtggctcct    660
gatatggcgc agcaatgcct ggcgtgggga gcgaactttg tcgctgttgg cgttgacacg    720
atgctctaca gcgatgccct ggatcaacga ctggcgatgt ttaaatcagg caaaaatggg    780
ccacgcataa aaggtagtta ttga                                            804

<210> SEQ ID NO 3
<211> LENGTH: 267
<212> TYPE: PRT
<213> ORGANISM: Escherichia coli
<220> FEATURE:
<223> OTHER INFORMATION: YfaU W23V

<400> SEQUENCE: 3

Met Asn Ala Leu Leu Ser Asn Pro Phe Lys Glu Arg Leu Arg Lys Gly
1               5                   10                  15

Glu Val Gln Ile Gly Leu Val Leu Ser Ser Thr Thr Ala Tyr Met Ala
            20                  25                  30

Glu Ile Ala Ala Thr Ser Gly Tyr Asp Trp Leu Leu Ile Asp Gly Glu
        35                  40                  45

His Ala Pro Asn Thr Ile Gln Asp Leu Tyr His Gln Leu Gln Ala Val
    50                  55                  60

Ala Pro Tyr Ala Ser Gln Pro Val Ile Arg Pro Val Glu Gly Ser Lys
65                  70                  75                  80

Pro Leu Ile Lys Gln Val Leu Asp Ile Gly Ala Gln Thr Leu Leu Ile
                85                  90                  95

Pro Met Val Asp Thr Ala Glu Gln Ala Arg Gln Val Val Ser Ala Thr
            100                 105                 110

Arg Tyr Pro Pro Tyr Gly Glu Arg Gly Val Gly Ala Ser Val Ala Arg
        115                 120                 125

Ala Ala Arg Trp Gly Arg Ile Glu Asn Tyr Met Ala Gln Val Asn Asp
    130                 135                 140

Ser Leu Cys Leu Leu Val Gln Val Glu Ser Lys Thr Ala Leu Asp Asn
145                 150                 155                 160

Leu Asp Glu Ile Leu Asp Val Glu Gly Ile Asp Gly Val Phe Ile Gly
                165                 170                 175

Pro Ala Asp Leu Ser Ala Ser Leu Gly Tyr Pro Asp Asn Ala Gly His
            180                 185                 190

Pro Glu Val Gln Arg Ile Ile Glu Thr Ser Ile Arg Arg Ile Arg Ala
        195                 200                 205

Ala Gly Lys Ala Ala Gly Phe Leu Ala Val Ala Pro Asp Met Ala Gln
    210                 215                 220

Gln Cys Leu Ala Trp Gly Ala Asn Phe Val Ala Val Gly Val Asp Thr
225                 230                 235                 240
```

Met Leu Tyr Ser Asp Ala Leu Asp Gln Arg Leu Ala Met Phe Lys Ser
            245                 250                 255

Gly Lys Asn Gly Pro Arg Ile Lys Gly Ser Tyr
        260                 265

<210> SEQ ID NO 4
<211> LENGTH: 267
<212> TYPE: PRT
<213> ORGANISM: Escherichia coli
<220> FEATURE:
<223> OTHER INFORMATION: YfaU L216A

<400> SEQUENCE: 4

Met Asn Ala Leu Leu Ser Asn Pro Phe Lys Glu Arg Leu Arg Lys Gly
1               5                   10                  15

Glu Val Gln Ile Gly Leu Trp Leu Ser Ser Thr Thr Ala Tyr Met Ala
            20                  25                  30

Glu Ile Ala Ala Thr Ser Gly Tyr Asp Trp Leu Leu Ile Asp Gly Glu
        35                  40                  45

His Ala Pro Asn Thr Ile Gln Asp Leu Tyr His Gln Leu Gln Ala Val
    50                  55                  60

Ala Pro Tyr Ala Ser Gln Pro Val Ile Arg Pro Val Glu Gly Ser Lys
65                  70                  75                  80

Pro Leu Ile Lys Gln Val Leu Asp Ile Gly Ala Gln Thr Leu Leu Ile
                85                  90                  95

Pro Met Val Asp Thr Ala Glu Gln Ala Arg Gln Val Val Ser Ala Thr
            100                 105                 110

Arg Tyr Pro Pro Tyr Gly Glu Arg Gly Val Gly Ala Ser Val Ala Arg
        115                 120                 125

Ala Ala Arg Trp Gly Arg Ile Glu Asn Tyr Met Ala Gln Val Asn Asp
    130                 135                 140

Ser Leu Cys Leu Leu Val Gln Val Glu Ser Lys Thr Ala Leu Asp Asn
145                 150                 155                 160

Leu Asp Glu Ile Leu Asp Val Glu Gly Ile Asp Gly Val Phe Ile Gly
                165                 170                 175

Pro Ala Asp Leu Ser Ala Ser Leu Gly Tyr Pro Asp Asn Ala Gly His
            180                 185                 190

Pro Glu Val Gln Arg Ile Ile Glu Thr Ser Ile Arg Arg Ile Arg Ala
        195                 200                 205

Ala Gly Lys Ala Ala Gly Phe Ala Ala Val Ala Pro Asp Met Ala Gln
    210                 215                 220

Gln Cys Leu Ala Trp Gly Ala Asn Phe Val Ala Val Gly Val Asp Thr
225                 230                 235                 240

Met Leu Tyr Ser Asp Ala Leu Asp Gln Arg Leu Ala Met Phe Lys Ser
            245                 250                 255

Gly Lys Asn Gly Pro Arg Ile Lys Gly Ser Tyr
        260                 265

<210> SEQ ID NO 5
<211> LENGTH: 267
<212> TYPE: PRT
<213> ORGANISM: Escherichia coli
<220> FEATURE:
<223> OTHER INFORMATION: YfaU W23V L216A

<400> SEQUENCE: 5

Met Asn Ala Leu Leu Ser Asn Pro Phe Lys Glu Arg Leu Arg Lys Gly
1               5                   10                  15

```
Glu Val Gln Ile Gly Leu Val Leu Ser Ser Thr Thr Ala Tyr Met Ala
            20                  25                  30

Glu Ile Ala Ala Thr Ser Gly Tyr Asp Trp Leu Leu Ile Asp Gly Glu
        35                  40                  45

His Ala Pro Asn Thr Ile Gln Asp Leu Tyr His Gln Leu Gln Ala Val
 50                  55                  60

Ala Pro Tyr Ala Ser Gln Pro Val Ile Arg Pro Val Glu Gly Ser Lys
 65                  70                  75                  80

Pro Leu Ile Lys Gln Val Leu Asp Ile Gly Ala Gln Thr Leu Leu Ile
                85                  90                  95

Pro Met Val Asp Thr Ala Glu Gln Ala Arg Gln Val Val Ser Ala Thr
                100                 105                 110

Arg Tyr Pro Pro Tyr Gly Glu Arg Gly Val Gly Ala Ser Val Ala Arg
            115                 120                 125

Ala Ala Arg Trp Gly Arg Ile Glu Asn Tyr Met Ala Gln Val Asn Asp
130                 135                 140

Ser Leu Cys Leu Leu Val Gln Val Glu Ser Lys Thr Ala Leu Asp Asn
145                 150                 155                 160

Leu Asp Glu Ile Leu Asp Val Glu Gly Ile Asp Gly Val Phe Ile Gly
                165                 170                 175

Pro Ala Asp Leu Ser Ala Ser Leu Gly Tyr Pro Asp Asn Ala Gly His
                180                 185                 190

Pro Glu Val Gln Arg Ile Ile Glu Thr Ser Ile Arg Arg Ile Arg Ala
            195                 200                 205

Ala Gly Lys Ala Ala Gly Phe Ala Ala Val Ala Pro Asp Met Ala Gln
210                 215                 220

Gln Cys Leu Ala Trp Gly Ala Asn Phe Val Ala Val Gly Val Asp Thr
225                 230                 235                 240

Met Leu Tyr Ser Asp Ala Leu Asp Gln Arg Leu Ala Met Phe Lys Ser
                245                 250                 255

Gly Lys Asn Gly Pro Arg Ile Lys Gly Ser Tyr
                260                 265

<210> SEQ ID NO 6
<211> LENGTH: 267
<212> TYPE: PRT
<213> ORGANISM: Escherichia coli
<220> FEATURE:
<223> OTHER INFORMATION: YfaU W23V F174V L216A

<400> SEQUENCE: 6

Met Asn Ala Leu Leu Ser Asn Pro Phe Lys Glu Arg Leu Arg Lys Gly
1               5                   10                  15

Glu Val Gln Ile Gly Leu Val Leu Ser Ser Thr Thr Ala Tyr Met Ala
            20                  25                  30

Glu Ile Ala Ala Thr Ser Gly Tyr Asp Trp Leu Leu Ile Asp Gly Glu
        35                  40                  45

His Ala Pro Asn Thr Ile Gln Asp Leu Tyr His Gln Leu Gln Ala Val
 50                  55                  60

Ala Pro Tyr Ala Ser Gln Pro Val Ile Arg Pro Val Glu Gly Ser Lys
 65                  70                  75                  80

Pro Leu Ile Lys Gln Val Leu Asp Ile Gly Ala Gln Thr Leu Leu Ile
                85                  90                  95

Pro Met Val Asp Thr Ala Glu Gln Ala Arg Gln Val Val Ser Ala Thr
                100                 105                 110
```

-continued

```
Arg Tyr Pro Pro Tyr Gly Glu Arg Gly Val Gly Ala Ser Val Ala Arg
            115                 120                 125

Ala Ala Arg Trp Gly Arg Ile Glu Asn Tyr Met Ala Gln Val Asn Asp
        130                 135                 140

Ser Leu Cys Leu Leu Val Gln Val Glu Ser Lys Thr Ala Leu Asp Asn
145                 150                 155                 160

Leu Asp Glu Ile Leu Asp Val Glu Gly Ile Asp Gly Val Val Ile Gly
                165                 170                 175

Pro Ala Asp Leu Ser Ala Ser Leu Gly Tyr Pro Asp Asn Ala Gly His
            180                 185                 190

Pro Glu Val Gln Arg Ile Ile Glu Thr Ser Ile Arg Arg Ile Arg Ala
        195                 200                 205

Ala Gly Lys Ala Ala Gly Phe Ala Ala Val Ala Pro Asp Met Ala Gln
    210                 215                 220

Gln Cys Leu Ala Trp Gly Ala Asn Phe Val Ala Val Gly Val Asp Thr
225                 230                 235                 240

Met Leu Tyr Ser Asp Ala Leu Asp Gln Arg Leu Ala Met Phe Lys Ser
                245                 250                 255

Gly Lys Asn Gly Pro Arg Ile Lys Gly Ser Tyr
            260                 265
```

<210> SEQ ID NO 7
<211> LENGTH: 267
<212> TYPE: PRT
<213> ORGANISM: Escherichia coli
<220> FEATURE:
<223> OTHER INFORMATION: YfaU W23A L216A

<400> SEQUENCE: 7

```
Met Asn Ala Leu Leu Ser Asn Pro Phe Lys Glu Arg Leu Arg Lys Gly
1               5                   10                  15

Glu Val Gln Ile Gly Leu Ala Leu Ser Ser Thr Thr Ala Tyr Met Ala
            20                  25                  30

Glu Ile Ala Ala Thr Ser Gly Tyr Asp Trp Leu Leu Ile Asp Gly Glu
        35                  40                  45

His Ala Pro Asn Thr Ile Gln Asp Leu Tyr His Gln Leu Gln Ala Val
    50                  55                  60

Ala Pro Tyr Ala Ser Gln Pro Val Ile Arg Pro Val Glu Gly Ser Lys
65                  70                  75                  80

Pro Leu Ile Lys Gln Val Leu Asp Ile Gly Ala Gln Thr Leu Leu Ile
                85                  90                  95

Pro Met Val Asp Thr Ala Glu Gln Ala Arg Gln Val Val Ser Ala Thr
            100                 105                 110

Arg Tyr Pro Pro Tyr Gly Glu Arg Gly Val Gly Ala Ser Val Ala Arg
        115                 120                 125

Ala Ala Arg Trp Gly Arg Ile Glu Asn Tyr Met Ala Gln Val Asn Asp
    130                 135                 140

Ser Leu Cys Leu Leu Val Gln Val Glu Ser Lys Thr Ala Leu Asp Asn
145                 150                 155                 160

Leu Asp Glu Ile Leu Asp Val Glu Gly Ile Asp Gly Val Phe Ile Gly
                165                 170                 175

Pro Ala Asp Leu Ser Ala Ser Leu Gly Tyr Pro Asp Asn Ala Gly His
            180                 185                 190

Pro Glu Val Gln Arg Ile Ile Glu Thr Ser Ile Arg Arg Ile Arg Ala
        195                 200                 205
```

```
Ala Gly Lys Ala Ala Gly Phe Ala Val Ala Pro Asp Met Ala Gln
        210                 215                 220

Gln Cys Leu Ala Trp Gly Ala Asn Phe Val Ala Val Gly Val Asp Thr
225                 230                 235                 240

Met Leu Tyr Ser Asp Ala Leu Asp Gln Arg Leu Ala Met Phe Lys Ser
                245                 250                 255

Gly Lys Asn Gly Pro Arg Ile Lys Gly Ser Tyr
        260                 265

<210> SEQ ID NO 8
<211> LENGTH: 367
<212> TYPE: PRT
<213> ORGANISM: Escherichia coli
<220> FEATURE:
<223> OTHER INFORMATION: Maltose binding protein or MBP

<400> SEQUENCE: 8

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300
```

-continued

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
            325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr
        355                 360                 365

<210> SEQ ID NO 9
<211> LENGTH: 649
<212> TYPE: PRT
<213> ORGANISM: Escherichia coli
<220> FEATURE:
<223> OTHER INFORMATION: MBP-YfaU
<220> FEATURE:
<221> NAME/KEY: PEPTIDE
<222> LOCATION: 464
<223> OTHER INFORMATION: MBP-YfaU with specific linker.

<400> SEQUENCE: 9

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp

```
            275                 280                 285
Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Ser
        355                 360                 365

Ser Gly Leu Glu Val Leu Phe Gln Gly Pro Ala Cys Gly Thr Met Asn
370                 375                 380

Ala Leu Leu Ser Asn Pro Phe Lys Glu Arg Leu Arg Lys Gly Glu Val
385                 390                 395                 400

Gln Ile Gly Leu Trp Leu Ser Ser Thr Thr Ala Tyr Met Ala Glu Ile
                405                 410                 415

Ala Ala Thr Ser Gly Tyr Asp Trp Leu Leu Ile Asp Gly Glu His Ala
            420                 425                 430

Pro Asn Thr Ile Gln Asp Leu Tyr His Gln Leu Gln Ala Val Ala Pro
        435                 440                 445

Tyr Ala Ser Gln Pro Val Ile Arg Pro Val Glu Gly Ser Lys Pro Leu
    450                 455                 460

Ile Lys Gln Val Leu Asp Ile Gly Ala Gln Thr Leu Leu Ile Pro Met
465                 470                 475                 480

Val Asp Thr Ala Glu Gln Ala Arg Gln Val Val Ser Ala Thr Arg Tyr
                485                 490                 495

Pro Pro Tyr Gly Glu Arg Gly Val Gly Ala Ser Val Ala Arg Ala Ala
            500                 505                 510

Arg Trp Gly Arg Ile Glu Asn Tyr Met Ala Gln Val Asn Asp Ser Leu
        515                 520                 525

Cys Leu Leu Val Gln Val Glu Ser Lys Thr Ala Leu Asp Asn Leu Asp
    530                 535                 540

Glu Ile Leu Asp Val Glu Gly Ile Asp Gly Val Phe Ile Gly Pro Ala
545                 550                 555                 560

Asp Leu Ser Ala Ser Leu Gly Tyr Pro Asp Asn Ala Gly His Pro Glu
                565                 570                 575

Val Gln Arg Ile Ile Glu Thr Ser Ile Arg Arg Ile Arg Ala Ala Gly
            580                 585                 590

Lys Ala Ala Gly Phe Leu Ala Val Ala Pro Asp Met Ala Gln Gln Cys
        595                 600                 605

Leu Ala Trp Gly Ala Asn Phe Val Ala Val Gly Val Asp Thr Met Leu
    610                 615                 620

Tyr Ser Asp Ala Leu Asp Gln Arg Leu Ala Met Phe Lys Ser Gly Lys
625                 630                 635                 640

Asn Gly Pro Arg Ile Lys Gly Ser Tyr
                645

<210> SEQ ID NO 10
<211> LENGTH: 663
<212> TYPE: PRT
<213> ORGANISM: Escherichia coli
<220> FEATURE:
<223> OTHER INFORMATION: MBP-YfaU of figure 4.
```

<400> SEQUENCE: 10

```
Met Arg Gly Ser His His His His His His Gly Ser Gly Ile Met Lys
1               5                   10                  15
Ile Glu Glu Gly Lys Leu Val Ile Trp Ile Asn Gly Asp Lys Gly Tyr
            20                  25                  30
Asn Gly Leu Ala Glu Val Gly Lys Phe Glu Lys Asp Thr Gly Ile
        35                  40                  45
Lys Val Thr Val Glu His Pro Asp Lys Leu Glu Lys Phe Pro Gln
    50                  55                  60
Val Ala Ala Thr Gly Asp Gly Pro Asp Ile Ile Phe Trp Ala His Asp
65                  70                  75                  80
Arg Phe Gly Gly Tyr Ala Gln Ser Gly Leu Leu Ala Glu Ile Thr Pro
            85                  90                  95
Asp Lys Ala Phe Gln Asp Lys Leu Tyr Pro Phe Thr Trp Asp Ala Val
            100                 105                 110
Arg Tyr Asn Gly Lys Leu Ile Ala Tyr Pro Ile Ala Val Glu Ala Leu
            115                 120                 125
Ser Leu Ile Tyr Asn Lys Asp Leu Leu Pro Asn Pro Pro Lys Thr Trp
    130                 135                 140
Glu Glu Ile Pro Ala Leu Asp Lys Glu Leu Lys Ala Lys Gly Lys Ser
145                 150                 155                 160
Ala Leu Met Phe Asn Leu Gln Glu Pro Tyr Phe Thr Trp Pro Leu Ile
                165                 170                 175
Ala Ala Asp Gly Gly Tyr Ala Phe Lys Tyr Glu Asn Gly Lys Tyr Asp
            180                 185                 190
Ile Lys Asp Val Gly Val Asp Asn Ala Gly Ala Lys Ala Gly Leu Thr
        195                 200                 205
Phe Leu Val Asp Leu Ile Lys Asn Lys His Met Asn Ala Asp Thr Asp
210                 215                 220
Tyr Ser Ile Ala Glu Ala Ala Phe Asn Lys Gly Glu Thr Ala Met Thr
225                 230                 235                 240
Ile Asn Gly Pro Trp Ala Trp Ser Asn Ile Asp Thr Ser Lys Val Asn
                245                 250                 255
Tyr Gly Val Thr Val Leu Pro Thr Phe Lys Gly Gln Pro Ser Lys Pro
            260                 265                 270
Phe Val Gly Val Leu Ser Ala Gly Ile Asn Ala Ala Ser Pro Asn Lys
        275                 280                 285
Glu Leu Ala Lys Glu Phe Leu Glu Asn Tyr Leu Leu Thr Asp Glu Gly
    290                 295                 300
Leu Glu Ala Val Asn Lys Asp Lys Pro Leu Gly Ala Val Ala Leu Lys
305                 310                 315                 320
Ser Tyr Glu Glu Glu Leu Ala Lys Asp Pro Arg Ile Ala Ala Thr Met
                325                 330                 335
Glu Asn Ala Gln Lys Gly Glu Ile Met Pro Asn Ile Pro Gln Met Ser
            340                 345                 350
Ala Phe Trp Tyr Ala Val Arg Thr Ala Val Ile Asn Ala Ala Ser Gly
        355                 360                 365
Arg Gln Thr Val Asp Glu Ala Leu Lys Asp Ala Gln Thr Ser Ser Gly
    370                 375                 380
Leu Glu Val Leu Phe Gln Gly Pro Ala Cys Gly Thr Met Asn Ala Leu
385                 390                 395                 400
Leu Ser Asn Pro Phe Lys Glu Arg Leu Arg Lys Gly Glu Val Gln Ile
            405                 410                 415
```

-continued

Gly Leu Trp Leu Ser Ser Thr Thr Ala Tyr Met Ala Glu Ile Ala Ala
            420                 425                 430

Thr Ser Gly Tyr Asp Trp Leu Leu Ile Asp Gly His Ala Pro Asn
        435                 440                 445

Thr Ile Gln Asp Leu Tyr His Gln Leu Gln Ala Val Ala Pro Tyr Ala
    450                 455                 460

Ser Gln Pro Val Ile Arg Pro Val Gly Ser Lys Pro Leu Ile Lys
465                 470                 475                 480

Gln Val Leu Asp Ile Gly Ala Gln Thr Leu Leu Ile Pro Met Val Asp
                485                 490                 495

Thr Ala Glu Gln Ala Arg Gln Val Val Ser Ala Thr Arg Tyr Pro Pro
            500                 505                 510

Tyr Gly Glu Arg Gly Val Gly Ala Ser Val Ala Arg Ala Ala Arg Trp
        515                 520                 525

Gly Arg Ile Glu Asn Tyr Met Ala Gln Val Asn Asp Ser Leu Cys Leu
    530                 535                 540

Leu Val Gln Val Glu Ser Lys Thr Ala Leu Asp Asn Leu Asp Glu Ile
545                 550                 555                 560

Leu Asp Val Glu Gly Ile Asp Gly Val Phe Ile Gly Pro Ala Asp Leu
                565                 570                 575

Ser Ala Ser Leu Gly Tyr Pro Asp Asn Ala Gly His Pro Glu Val Gln
            580                 585                 590

Arg Ile Ile Glu Thr Ser Ile Arg Arg Ile Arg Ala Ala Gly Lys Ala
        595                 600                 605

Ala Gly Phe Leu Ala Val Ala Pro Asp Met Ala Gln Gln Cys Leu Ala
    610                 615                 620

Trp Gly Ala Asn Phe Val Ala Val Gly Val Asp Thr Met Leu Tyr Ser
625                 630                 635                 640

Asp Ala Leu Asp Gln Arg Leu Ala Met Phe Lys Ser Gly Lys Asn Gly
                645                 650                 655

Pro Arg Ile Lys Gly Ser Tyr
            660

<210> SEQ ID NO 11
<211> LENGTH: 35
<212> TYPE: DNA
<213> ORGANISM: Escherichia coli
<220> FEATURE:
<223> OTHER INFORMATION: MBP-3C forward primer

<400> SEQUENCE: 11
gctagcggat ccggcatcat gaaaatcgaa gaagg                                    35

<210> SEQ ID NO 12
<211> LENGTH: 34
<212> TYPE: DNA
<213> ORGANISM: Escherichia coli
<220> FEATURE:
<223> OTHER INFORMATION: MBP-3C reverse primer

<400> SEQUENCE: 12
gctagcgcat gccggaccct gaaacagaac ttcc                                    34

<210> SEQ ID NO 13
<211> LENGTH: 663
<212> TYPE: PRT
<213> ORGANISM: Escherichia coli
<220> FEATURE:

<223> OTHER INFORMATION: MBP-YfaU W23V

<400> SEQUENCE: 13

```
Met Arg Gly Ser His His His His His His Gly Ser Gly Ile Met Lys
1               5                   10                  15

Ile Glu Glu Gly Lys Leu Val Ile Trp Ile Asn Gly Asp Lys Gly Tyr
            20                  25                  30

Asn Gly Leu Ala Glu Val Gly Lys Lys Phe Glu Lys Asp Thr Gly Ile
        35                  40                  45

Lys Val Thr Val Glu His Pro Asp Lys Leu Glu Glu Lys Phe Pro Gln
    50                  55                  60

Val Ala Ala Thr Gly Asp Gly Pro Asp Ile Ile Phe Trp Ala His Asp
65                  70                  75                  80

Arg Phe Gly Gly Tyr Ala Gln Ser Gly Leu Leu Ala Glu Ile Thr Pro
                85                  90                  95

Asp Lys Ala Phe Gln Asp Lys Leu Tyr Pro Phe Thr Trp Asp Ala Val
            100                 105                 110

Arg Tyr Asn Gly Lys Leu Ile Ala Tyr Pro Ile Ala Val Glu Ala Leu
        115                 120                 125

Ser Leu Ile Tyr Asn Lys Asp Leu Leu Pro Asn Pro Pro Lys Thr Trp
    130                 135                 140

Glu Glu Ile Pro Ala Leu Asp Lys Glu Leu Lys Ala Lys Gly Lys Ser
145                 150                 155                 160

Ala Leu Met Phe Asn Leu Gln Glu Pro Tyr Phe Thr Trp Pro Leu Ile
                165                 170                 175

Ala Ala Asp Gly Gly Tyr Ala Phe Lys Tyr Glu Asn Gly Lys Tyr Asp
            180                 185                 190

Ile Lys Asp Val Gly Val Asp Asn Ala Gly Ala Lys Ala Gly Leu Thr
        195                 200                 205

Phe Leu Val Asp Leu Ile Lys Asn Lys His Met Asn Ala Asp Thr Asp
    210                 215                 220

Tyr Ser Ile Ala Glu Ala Ala Phe Asn Lys Gly Glu Thr Ala Met Thr
225                 230                 235                 240

Ile Asn Gly Pro Trp Ala Trp Ser Asn Ile Asp Thr Ser Lys Val Asn
                245                 250                 255

Tyr Gly Val Thr Val Leu Pro Thr Phe Lys Gly Gln Pro Ser Lys Pro
            260                 265                 270

Phe Val Gly Val Leu Ser Ala Gly Ile Asn Ala Ala Ser Pro Asn Lys
        275                 280                 285

Glu Leu Ala Lys Glu Phe Leu Glu Asn Tyr Leu Leu Thr Asp Glu Gly
    290                 295                 300

Leu Glu Ala Val Asn Lys Asp Lys Pro Leu Gly Ala Val Ala Leu Lys
305                 310                 315                 320

Ser Tyr Glu Glu Glu Leu Ala Lys Asp Pro Arg Ile Ala Ala Thr Met
                325                 330                 335

Glu Asn Ala Gln Lys Gly Glu Ile Met Pro Asn Ile Pro Gln Met Ser
            340                 345                 350

Ala Phe Trp Tyr Ala Val Arg Thr Ala Val Ile Asn Ala Ala Ser Gly
        355                 360                 365

Arg Gln Thr Val Asp Glu Ala Leu Lys Asp Ala Gln Thr Ser Ser Gly
    370                 375                 380

Leu Glu Val Leu Phe Gln Gly Pro Ala Cys Gly Thr Met Asn Ala Leu
385                 390                 395                 400
```

Leu Ser Asn Pro Phe Lys Glu Arg Leu Arg Lys Gly Glu Val Gln Ile
                405                 410                 415

Gly Leu Val Leu Ser Ser Thr Thr Ala Tyr Met Ala Glu Ile Ala Ala
            420                 425                 430

Thr Ser Gly Tyr Asp Trp Leu Leu Ile Asp Gly Glu His Ala Pro Asn
            435                 440                 445

Thr Ile Gln Asp Leu Tyr His Gln Leu Gln Ala Val Ala Pro Tyr Ala
        450                 455                 460

Ser Gln Pro Val Ile Arg Pro Val Glu Gly Ser Lys Pro Leu Ile Lys
465                 470                 475                 480

Gln Val Leu Asp Ile Gly Ala Gln Thr Leu Leu Ile Pro Met Val Asp
                485                 490                 495

Thr Ala Glu Gln Ala Arg Gln Val Val Ser Ala Thr Arg Tyr Pro Pro
            500                 505                 510

Tyr Gly Glu Arg Gly Val Gly Ala Ser Val Ala Arg Ala Ala Arg Trp
            515                 520                 525

Gly Arg Ile Glu Asn Tyr Met Ala Gln Val Asn Asp Ser Leu Cys Leu
            530                 535                 540

Leu Val Gln Val Glu Ser Lys Thr Ala Leu Asp Asn Leu Asp Glu Ile
545                 550                 555                 560

Leu Asp Val Glu Gly Ile Asp Gly Val Phe Ile Gly Pro Ala Asp Leu
                565                 570                 575

Ser Ala Ser Leu Gly Tyr Pro Asp Asn Ala Gly His Pro Glu Val Gln
            580                 585                 590

Arg Ile Ile Glu Thr Ser Ile Arg Arg Ile Arg Ala Ala Gly Lys Ala
            595                 600                 605

Ala Gly Phe Leu Ala Val Ala Pro Asp Met Ala Gln Gln Cys Leu Ala
        610                 615                 620

Trp Gly Ala Asn Phe Val Ala Val Gly Val Asp Thr Met Leu Tyr Ser
625                 630                 635                 640

Asp Ala Leu Asp Gln Arg Leu Ala Met Phe Lys Ser Gly Lys Asn Gly
                645                 650                 655

Pro Arg Ile Lys Gly Ser Tyr
            660

<210> SEQ ID NO 14
<211> LENGTH: 663
<212> TYPE: PRT
<213> ORGANISM: Escherichia coli
<220> FEATURE:
<223> OTHER INFORMATION: MBP-YfaU L216A

<400> SEQUENCE: 14

Met Arg Gly Ser His His His His His His Gly Ser Gly Ile Met Lys
1               5                   10                  15

Ile Glu Glu Gly Lys Leu Val Ile Trp Ile Asn Gly Asp Lys Gly Tyr
                20                  25                  30

Asn Gly Leu Ala Glu Val Gly Lys Lys Phe Glu Lys Asp Thr Gly Ile
            35                  40                  45

Lys Val Thr Val Glu His Pro Asp Lys Leu Glu Glu Lys Phe Pro Gln
        50                  55                  60

Val Ala Ala Thr Gly Asp Gly Pro Asp Ile Ile Phe Trp Ala His Asp
65                  70                  75                  80

Arg Phe Gly Gly Tyr Ala Gln Ser Gly Leu Leu Ala Glu Ile Thr Pro
                85                  90                  95

```
Asp Lys Ala Phe Gln Asp Lys Leu Tyr Pro Phe Thr Trp Asp Ala Val
            100                 105                 110
Arg Tyr Asn Gly Lys Leu Ile Ala Tyr Pro Ile Ala Val Glu Ala Leu
        115                 120                 125
Ser Leu Ile Tyr Asn Lys Asp Leu Leu Pro Asn Pro Pro Lys Thr Trp
    130                 135                 140
Glu Glu Ile Pro Ala Leu Asp Lys Glu Leu Lys Ala Lys Gly Lys Ser
145                 150                 155                 160
Ala Leu Met Phe Asn Leu Gln Glu Pro Tyr Phe Thr Trp Pro Leu Ile
                165                 170                 175
Ala Ala Asp Gly Gly Tyr Ala Phe Lys Tyr Glu Asn Gly Lys Tyr Asp
            180                 185                 190
Ile Lys Asp Val Gly Val Asp Asn Ala Gly Ala Lys Ala Gly Leu Thr
        195                 200                 205
Phe Leu Val Asp Leu Ile Lys Asn Lys His Met Asn Ala Asp Thr Asp
    210                 215                 220
Tyr Ser Ile Ala Glu Ala Ala Phe Asn Lys Gly Glu Thr Ala Met Thr
225                 230                 235                 240
Ile Asn Gly Pro Trp Ala Trp Ser Asn Ile Asp Thr Ser Lys Val Asn
                245                 250                 255
Tyr Gly Val Thr Val Leu Pro Thr Phe Lys Gly Gln Pro Ser Lys Pro
            260                 265                 270
Phe Val Gly Val Leu Ser Ala Gly Ile Asn Ala Ala Ser Pro Asn Lys
        275                 280                 285
Glu Leu Ala Lys Glu Phe Leu Glu Asn Tyr Leu Leu Thr Asp Glu Gly
    290                 295                 300
Leu Glu Ala Val Asn Lys Asp Lys Pro Leu Gly Ala Val Ala Leu Lys
305                 310                 315                 320
Ser Tyr Glu Glu Glu Leu Ala Lys Asp Pro Arg Ile Ala Ala Thr Met
                325                 330                 335
Glu Asn Ala Gln Lys Gly Glu Ile Met Pro Asn Ile Pro Gln Met Ser
            340                 345                 350
Ala Phe Trp Tyr Ala Val Arg Thr Ala Val Ile Asn Ala Ala Ser Gly
        355                 360                 365
Arg Gln Thr Val Asp Glu Ala Leu Lys Asp Ala Gln Thr Ser Ser Gly
    370                 375                 380
Leu Glu Val Leu Phe Gln Gly Pro Ala Cys Gly Thr Met Asn Ala Leu
385                 390                 395                 400
Leu Ser Asn Pro Phe Lys Glu Arg Leu Arg Lys Gly Glu Val Gln Ile
                405                 410                 415
Gly Leu Trp Leu Ser Ser Thr Thr Ala Tyr Met Ala Glu Ile Ala Ala
            420                 425                 430
Thr Ser Gly Tyr Asp Trp Leu Leu Ile Asp Gly Glu His Ala Pro Asn
        435                 440                 445
Thr Ile Gln Asp Leu Tyr His Gln Leu Gln Ala Val Ala Pro Tyr Ala
    450                 455                 460
Ser Gln Pro Val Ile Arg Pro Val Glu Gly Ser Lys Pro Leu Ile Lys
465                 470                 475                 480
Gln Val Leu Asp Ile Gly Ala Gln Thr Leu Leu Ile Pro Met Val Asp
                485                 490                 495
Thr Ala Glu Gln Ala Arg Gln Val Val Ser Ala Thr Arg Tyr Pro Pro
            500                 505                 510
Tyr Gly Glu Arg Gly Val Gly Ala Ser Val Ala Arg Ala Ala Arg Trp
```

-continued

```
                515                 520                 525
Gly Arg Ile Glu Asn Tyr Met Ala Gln Val Asn Asp Ser Leu Cys Leu
530                 535                 540

Leu Val Gln Val Glu Ser Lys Thr Ala Leu Asp Asn Leu Asp Glu Ile
545                 550                 555                 560

Leu Asp Val Glu Gly Ile Asp Gly Val Phe Ile Gly Pro Ala Asp Leu
                565                 570                 575

Ser Ala Ser Leu Gly Tyr Pro Asp Asn Ala Gly His Pro Glu Val Gln
                580                 585                 590

Arg Ile Ile Glu Thr Ser Ile Arg Arg Ile Arg Ala Ala Gly Lys Ala
                595                 600                 605

Ala Gly Phe Ala Ala Val Ala Pro Asp Met Ala Gln Gln Cys Leu Ala
                610                 615                 620

Trp Gly Ala Asn Phe Val Ala Val Gly Val Asp Thr Met Leu Tyr Ser
625                 630                 635                 640

Asp Ala Leu Asp Gln Arg Leu Ala Met Phe Lys Ser Gly Lys Asn Gly
                645                 650                 655

Pro Arg Ile Lys Gly Ser Tyr
                660

<210> SEQ ID NO 15
<211> LENGTH: 663
<212> TYPE: PRT
<213> ORGANISM: Escherichia coli
<220> FEATURE:
<223> OTHER INFORMATION: MBP-YfaU W23V L216A

<400> SEQUENCE: 15

Met Arg Gly Ser His His His His His His Gly Ser Gly Ile Met Lys
1               5                   10                  15

Ile Glu Glu Gly Lys Leu Val Ile Trp Ile Asn Gly Asp Lys Gly Tyr
                20                  25                  30

Asn Gly Leu Ala Glu Val Gly Lys Lys Phe Glu Lys Asp Thr Gly Ile
                35                  40                  45

Lys Val Thr Val Glu His Pro Asp Lys Leu Glu Glu Lys Phe Pro Gln
50                  55                  60

Val Ala Ala Thr Gly Asp Gly Pro Asp Ile Ile Phe Trp Ala His Asp
65                  70                  75                  80

Arg Phe Gly Gly Tyr Ala Gln Ser Gly Leu Leu Ala Glu Ile Thr Pro
                85                  90                  95

Asp Lys Ala Phe Gln Asp Lys Leu Tyr Pro Phe Thr Trp Asp Ala Val
                100                 105                 110

Arg Tyr Asn Gly Lys Leu Ile Ala Tyr Pro Ile Ala Val Glu Ala Leu
                115                 120                 125

Ser Leu Ile Tyr Asn Lys Asp Leu Leu Pro Asn Pro Pro Lys Thr Trp
130                 135                 140

Glu Glu Ile Pro Ala Leu Asp Lys Glu Leu Lys Ala Lys Gly Lys Ser
145                 150                 155                 160

Ala Leu Met Phe Asn Leu Gln Glu Pro Tyr Phe Thr Trp Pro Leu Ile
                165                 170                 175

Ala Ala Asp Gly Gly Tyr Ala Phe Lys Tyr Glu Asn Gly Lys Tyr Asp
                180                 185                 190

Ile Lys Asp Val Gly Val Asp Asn Ala Gly Ala Lys Ala Gly Leu Thr
                195                 200                 205

Phe Leu Val Asp Leu Ile Lys Asn Lys His Met Asn Ala Asp Thr Asp
```

-continued

```
            210                 215                 220
Tyr Ser Ile Ala Glu Ala Ala Phe Asn Lys Gly Glu Thr Ala Met Thr
225                 230                 235                 240

Ile Asn Gly Pro Trp Ala Trp Ser Asn Ile Asp Thr Ser Lys Val Asn
                245                 250                 255

Tyr Gly Val Thr Val Leu Pro Thr Phe Lys Gly Gln Pro Ser Lys Pro
                260                 265                 270

Phe Val Gly Val Leu Ser Ala Gly Ile Asn Ala Ala Ser Pro Asn Lys
                275                 280                 285

Glu Leu Ala Lys Glu Phe Leu Glu Asn Tyr Leu Leu Thr Asp Glu Gly
        290                 295                 300

Leu Glu Ala Val Asn Lys Asp Lys Pro Leu Gly Ala Val Ala Leu Lys
305                 310                 315                 320

Ser Tyr Glu Glu Glu Leu Ala Lys Asp Pro Arg Ile Ala Ala Thr Met
                325                 330                 335

Glu Asn Ala Gln Lys Gly Glu Ile Met Pro Asn Ile Pro Gln Met Ser
                340                 345                 350

Ala Phe Trp Tyr Ala Val Arg Thr Ala Val Ile Asn Ala Ala Ser Gly
                355                 360                 365

Arg Gln Thr Val Asp Glu Ala Leu Lys Asp Ala Gln Thr Ser Ser Gly
        370                 375                 380

Leu Glu Val Leu Phe Gln Gly Pro Ala Cys Gly Thr Met Asn Ala Leu
385                 390                 395                 400

Leu Ser Asn Pro Phe Lys Glu Arg Leu Arg Lys Gly Glu Val Gln Ile
                405                 410                 415

Gly Leu Val Leu Ser Thr Thr Ala Tyr Met Ala Glu Ile Ala Ala
                420                 425                 430

Thr Ser Gly Tyr Asp Trp Leu Leu Ile Asp Gly Glu His Ala Pro Asn
                435                 440                 445

Thr Ile Gln Asp Leu Tyr His Gln Leu Gln Ala Val Ala Pro Tyr Ala
        450                 455                 460

Ser Gln Pro Val Ile Arg Pro Val Glu Gly Ser Lys Pro Leu Ile Lys
465                 470                 475                 480

Gln Val Leu Asp Ile Gly Ala Gln Thr Leu Leu Ile Pro Met Val Asp
                485                 490                 495

Thr Ala Glu Gln Ala Arg Gln Val Val Ser Ala Thr Arg Tyr Pro Pro
                500                 505                 510

Tyr Gly Glu Arg Gly Val Gly Ala Ser Val Ala Arg Ala Ala Arg Trp
                515                 520                 525

Gly Arg Ile Glu Asn Tyr Met Ala Gln Val Asn Asp Ser Leu Cys Leu
        530                 535                 540

Leu Val Gln Val Glu Ser Lys Thr Ala Leu Asp Asn Leu Asp Glu Ile
545                 550                 555                 560

Leu Asp Val Glu Gly Ile Asp Gly Val Phe Ile Gly Pro Ala Asp Leu
                565                 570                 575

Ser Ala Ser Leu Gly Tyr Pro Asp Asn Ala Gly His Pro Glu Val Gln
                580                 585                 590

Arg Ile Ile Glu Thr Ser Ile Arg Arg Ile Arg Ala Ala Gly Lys Ala
        595                 600                 605

Ala Gly Phe Ala Ala Val Ala Pro Asp Met Ala Gln Gln Cys Leu Ala
610                 615                 620

Trp Gly Ala Asn Phe Val Ala Val Gly Val Asp Thr Met Leu Tyr Ser
625                 630                 635                 640
```

-continued

Asp Ala Leu Asp Gln Arg Leu Ala Met Phe Lys Ser Gly Lys Asn Gly
            645                 650                 655

Pro Arg Ile Lys Gly Ser Tyr
            660

<210> SEQ ID NO 16
<211> LENGTH: 663
<212> TYPE: PRT
<213> ORGANISM: Escherichia coli
<220> FEATURE:
<223> OTHER INFORMATION: MBP- YfaU W23V F174V L216A

<400> SEQUENCE: 16

Met Arg Gly Ser His His His His His Gly Ser Gly Ile Met Lys
1               5                   10                  15

Ile Glu Glu Gly Lys Leu Val Ile Trp Ile Asn Gly Asp Lys Gly Tyr
                20                  25                  30

Asn Gly Leu Ala Glu Val Gly Lys Lys Phe Glu Lys Asp Thr Gly Ile
            35                  40                  45

Lys Val Thr Val Glu His Pro Asp Lys Leu Glu Glu Lys Phe Pro Gln
50                  55                  60

Val Ala Ala Thr Gly Asp Gly Pro Asp Ile Ile Phe Trp Ala His Asp
65                  70                  75                  80

Arg Phe Gly Gly Tyr Ala Gln Ser Gly Leu Leu Ala Glu Ile Thr Pro
                85                  90                  95

Asp Lys Ala Phe Gln Asp Lys Leu Tyr Pro Phe Thr Trp Asp Ala Val
            100                 105                 110

Arg Tyr Asn Gly Lys Leu Ile Ala Tyr Pro Ile Ala Val Glu Ala Leu
        115                 120                 125

Ser Leu Ile Tyr Asn Lys Asp Leu Leu Pro Asn Pro Pro Lys Thr Trp
    130                 135                 140

Glu Glu Ile Pro Ala Leu Asp Lys Glu Leu Lys Ala Lys Gly Lys Ser
145                 150                 155                 160

Ala Leu Met Phe Asn Leu Gln Glu Pro Tyr Phe Thr Trp Pro Leu Ile
                165                 170                 175

Ala Ala Asp Gly Gly Tyr Ala Phe Lys Tyr Glu Asn Gly Lys Tyr Asp
            180                 185                 190

Ile Lys Asp Val Gly Val Asp Asn Ala Gly Ala Lys Ala Gly Leu Thr
        195                 200                 205

Phe Leu Val Asp Leu Ile Lys Asn Lys His Met Asn Ala Asp Thr Asp
    210                 215                 220

Tyr Ser Ile Ala Glu Ala Ala Phe Asn Lys Gly Glu Thr Ala Met Thr
225                 230                 235                 240

Ile Asn Gly Pro Trp Ala Trp Ser Asn Ile Asp Thr Ser Lys Val Asn
                245                 250                 255

Tyr Gly Val Thr Val Leu Pro Thr Phe Lys Gly Gln Pro Ser Lys Pro
            260                 265                 270

Phe Val Gly Val Leu Ser Ala Gly Ile Asn Ala Ala Ser Pro Asn Lys
        275                 280                 285

Glu Leu Ala Lys Glu Phe Leu Glu Asn Tyr Leu Leu Thr Asp Glu Gly
    290                 295                 300

Leu Glu Ala Val Asn Lys Asp Lys Pro Leu Gly Ala Val Ala Leu Lys
305                 310                 315                 320

Ser Tyr Glu Glu Glu Leu Ala Lys Asp Pro Arg Ile Ala Ala Thr Met
                325                 330                 335

Glu Asn Ala Gln Lys Gly Glu Ile Met Pro Asn Ile Pro Gln Met Ser
                340                 345                 350

Ala Phe Trp Tyr Ala Val Arg Thr Ala Val Ile Asn Ala Ala Ser Gly
            355                 360                 365

Arg Gln Thr Val Asp Glu Ala Leu Lys Asp Ala Gln Thr Ser Ser Gly
        370                 375                 380

Leu Glu Val Leu Phe Gln Gly Pro Ala Cys Gly Thr Met Asn Ala Leu
385                 390                 395                 400

Leu Ser Asn Pro Phe Lys Glu Arg Leu Arg Lys Gly Glu Val Gln Ile
                405                 410                 415

Gly Leu Val Leu Ser Ser Thr Thr Ala Tyr Met Ala Glu Ile Ala Ala
            420                 425                 430

Thr Ser Gly Tyr Asp Trp Leu Leu Ile Asp Gly Glu His Ala Pro Asn
        435                 440                 445

Thr Ile Gln Asp Leu Tyr His Gln Leu Gln Ala Val Ala Pro Tyr Ala
450                 455                 460

Ser Gln Pro Val Ile Arg Pro Val Glu Gly Ser Lys Pro Leu Ile Lys
465                 470                 475                 480

Gln Val Leu Asp Ile Gly Ala Gln Thr Leu Leu Ile Pro Met Val Asp
                485                 490                 495

Thr Ala Glu Gln Ala Arg Gln Val Val Ser Ala Thr Arg Tyr Pro Pro
            500                 505                 510

Tyr Gly Glu Arg Gly Val Gly Ala Ser Val Ala Arg Ala Ala Arg Trp
        515                 520                 525

Gly Arg Ile Glu Asn Tyr Met Ala Gln Val Asn Asp Ser Leu Cys Leu
        530                 535                 540

Leu Val Gln Val Glu Ser Lys Thr Ala Leu Asp Asn Leu Asp Glu Ile
545                 550                 555                 560

Leu Asp Val Glu Gly Ile Asp Gly Val Ile Gly Pro Ala Asp Leu
                565                 570                 575

Ser Ala Ser Leu Gly Tyr Pro Asp Asn Ala Gly His Pro Glu Val Gln
            580                 585                 590

Arg Ile Ile Glu Thr Ser Ile Arg Arg Ile Arg Ala Ala Gly Lys Ala
        595                 600                 605

Ala Gly Phe Ala Ala Val Ala Pro Asp Met Ala Gln Gln Cys Leu Ala
        610                 615                 620

Trp Gly Ala Asn Phe Val Ala Val Gly Val Asp Thr Met Leu Tyr Ser
625                 630                 635                 640

Asp Ala Leu Asp Gln Arg Leu Ala Met Phe Lys Ser Gly Lys Asn Gly
                645                 650                 655

Pro Arg Ile Lys Gly Ser Tyr
            660

<210> SEQ ID NO 17
<211> LENGTH: 663
<212> TYPE: PRT
<213> ORGANISM: Escherichia coli
<220> FEATURE:
<223> OTHER INFORMATION: MBP- YfaU W23A L216A

<400> SEQUENCE: 17

Met Arg Gly Ser His His His His His His Gly Ser Gly Ile Met Lys
1               5                   10                  15

Ile Glu Glu Gly Lys Leu Val Ile Trp Ile Asn Gly Asp Lys Gly Tyr
                20                  25                  30

-continued

```
Asn Gly Leu Ala Glu Val Gly Lys Lys Phe Glu Lys Asp Thr Gly Ile
         35                  40                  45
Lys Val Thr Val Glu His Pro Asp Lys Leu Glu Glu Lys Phe Pro Gln
 50                  55                  60
Val Ala Ala Thr Gly Asp Gly Pro Asp Ile Ile Phe Trp Ala His Asp
 65                  70                  75                  80
Arg Phe Gly Gly Tyr Ala Gln Ser Gly Leu Leu Ala Glu Ile Thr Pro
                 85                  90                  95
Asp Lys Ala Phe Gln Asp Lys Leu Tyr Pro Phe Thr Trp Asp Ala Val
                100                 105                 110
Arg Tyr Asn Gly Lys Leu Ile Ala Tyr Pro Ile Ala Val Glu Ala Leu
            115                 120                 125
Ser Leu Ile Tyr Asn Lys Asp Leu Leu Pro Asn Pro Pro Lys Thr Trp
        130                 135                 140
Glu Glu Ile Pro Ala Leu Asp Lys Glu Leu Lys Ala Lys Gly Lys Ser
145                 150                 155                 160
Ala Leu Met Phe Asn Leu Gln Glu Pro Tyr Phe Thr Trp Pro Leu Ile
                165                 170                 175
Ala Ala Asp Gly Gly Tyr Ala Phe Lys Tyr Glu Asn Gly Lys Tyr Asp
            180                 185                 190
Ile Lys Asp Val Gly Val Asp Asn Ala Gly Ala Lys Ala Gly Leu Thr
        195                 200                 205
Phe Leu Val Asp Leu Ile Lys Asn Lys His Met Asn Ala Asp Thr Asp
    210                 215                 220
Tyr Ser Ile Ala Glu Ala Ala Phe Asn Lys Gly Glu Thr Ala Met Thr
225                 230                 235                 240
Ile Asn Gly Pro Trp Ala Trp Ser Asn Ile Asp Thr Ser Lys Val Asn
                245                 250                 255
Tyr Gly Val Thr Val Leu Pro Thr Phe Lys Gly Gln Pro Ser Lys Pro
            260                 265                 270
Phe Val Gly Val Leu Ser Ala Gly Ile Asn Ala Ala Ser Pro Asn Lys
        275                 280                 285
Glu Leu Ala Lys Glu Phe Leu Glu Asn Tyr Leu Leu Thr Asp Glu Gly
    290                 295                 300
Leu Glu Ala Val Asn Lys Asp Lys Pro Leu Gly Ala Val Ala Leu Lys
305                 310                 315                 320
Ser Tyr Glu Glu Glu Leu Ala Lys Asp Pro Arg Ile Ala Ala Thr Met
                325                 330                 335
Glu Asn Ala Gln Lys Gly Glu Ile Met Pro Asn Ile Pro Gln Met Ser
            340                 345                 350
Ala Phe Trp Tyr Ala Val Arg Thr Ala Val Ile Asn Ala Ala Ser Gly
        355                 360                 365
Arg Gln Thr Val Asp Glu Ala Leu Lys Asp Ala Gln Thr Ser Ser Gly
    370                 375                 380
Leu Glu Val Leu Phe Gln Gly Pro Ala Cys Gly Thr Met Asn Ala Leu
385                 390                 395                 400
Leu Ser Asn Pro Phe Lys Glu Arg Leu Arg Lys Gly Glu Val Gln Ile
                405                 410                 415
Gly Leu Ala Leu Ser Ser Thr Thr Ala Tyr Met Ala Glu Ile Ala Ala
            420                 425                 430
Thr Ser Gly Tyr Asp Trp Leu Leu Ile Asp Gly Glu His Ala Pro Asn
        435                 440                 445
```

```
Thr Ile Gln Asp Leu Tyr His Gln Leu Gln Ala Val Ala Pro Tyr Ala
    450             455             460

Ser Gln Pro Val Ile Arg Pro Val Glu Gly Ser Lys Pro Leu Ile Lys
465             470             475             480

Gln Val Leu Asp Ile Gly Ala Gln Thr Leu Leu Ile Pro Met Val Asp
            485             490             495

Thr Ala Glu Gln Ala Arg Gln Val Val Ser Ala Thr Arg Tyr Pro Pro
            500             505             510

Tyr Gly Glu Arg Gly Val Gly Ala Ser Val Ala Arg Ala Ala Arg Trp
        515             520             525

Gly Arg Ile Glu Asn Tyr Met Ala Gln Val Asn Asp Ser Leu Cys Leu
    530             535             540

Leu Val Gln Val Glu Ser Lys Thr Ala Leu Asp Asn Leu Asp Glu Ile
545             550             555             560

Leu Asp Val Glu Gly Ile Asp Gly Val Phe Ile Gly Pro Ala Asp Leu
            565             570             575

Ser Ala Ser Leu Gly Tyr Pro Asp Asn Ala Gly His Pro Glu Val Gln
            580             585             590

Arg Ile Ile Glu Thr Ser Ile Arg Arg Ile Arg Ala Ala Gly Lys Ala
        595             600             605

Ala Gly Phe Ala Ala Val Ala Pro Asp Met Ala Gln Gln Cys Leu Ala
    610             615             620

Trp Gly Ala Asn Phe Val Ala Val Gly Val Asp Thr Met Leu Tyr Ser
625             630             635             640

Asp Ala Leu Asp Gln Arg Leu Ala Met Phe Lys Ser Gly Lys Asn Gly
            645             650             655

Pro Arg Ile Lys Gly Ser Tyr
            660
```